United States Patent [19]

Marangos et al.

[11] Patent Number: 6,063,819
[45] Date of Patent: May 16, 2000

[54] NEUROPROTECTIVE POLY-GUANIDINO COMPOUNDS WHICH BLOCK PRESYNAPTIC N AND P/Q CALCIUM CHANNELS

[75] Inventors: Paul J. Marangos, La Costa; Brian W. Sullivan, Escondido; Torsten Wiemann, La Costa; Anne M. Danks, Solana Beach; Marina Sragovicz, San Diego; Lewis R. Makings, Encinitas, all of Calif.

[73] Assignee: Cypros Pharmaceutical Corp., Carlsbad, Calif.

[21] Appl. No.: 09/026,415

[22] Filed: Feb. 18, 1998

Related U.S. Application Data

[63] Continuation-in-part of application No. 08/804,213, Feb. 21, 1997, abandoned.

[51] Int. Cl.[7] .......................... A61K 31/55; C07C 233/05
[52] U.S. Cl. .......................... 514/634; 514/616; 564/157; 564/48; 564/50; 564/51; 564/148; 564/151; 564/155; 564/227
[58] Field of Search .................... 514/634, 616; 564/157, 45, 50, 51, 148, 151, 155, 227

[56] References Cited

U.S. PATENT DOCUMENTS

| | | | |
|---|---|---|---|
| 4,709,094 | 11/1987 | Weber et al. | 564/238 |
| 4,906,779 | 3/1990 | Weber et al. | 564/238 |
| 4,925,664 | 5/1990 | Jackson et al. | 424/537 |
| 4,950,739 | 8/1990 | Cherksey et al. | 530/350 |
| 5,037,846 | 8/1991 | Saccomano et al. | 514/419 |
| 5,093,525 | 3/1992 | Weber et al. | 563/238 |
| 5,122,596 | 6/1992 | Phillips et al. | 530/350 |
| 5,190,976 | 3/1993 | Weber et al. | 514/634 |
| 5,227,397 | 7/1993 | Saccomano et al. | 514/419 |
| 5,242,947 | 9/1993 | Cherksey et al. | 514/626 |
| 5,262,568 | 11/1993 | Weber et al. | 564/238 |
| 5,403,861 | 4/1995 | Goldin et al. | . |
| 5,438,130 | 8/1995 | Goldin et al. | 536/27.81 |
| 5,599,984 | 2/1997 | Bianchi et al. | 564/157 |
| 5,614,630 | 3/1997 | Goldin et al. | . |
| 5,622,968 | 4/1997 | Goldin et al. | 514/313 |
| 5,637,623 | 6/1997 | Goldin et al. | 514/634 |
| 5,652,269 | 7/1997 | Goldin et al. | 514/632 |
| 5,670,519 | 9/1997 | Goldin et al. | 514/313 |
| 5,672,608 | 9/1997 | Goldin et al. | 514/313 |
| 5,677,348 | 10/1997 | Goldin et al. | 514/634 |
| 5,681,861 | 10/1997 | Goldin et al. | 514/634 |
| 5,686,495 | 11/1997 | Goldin et al. | 514/632 |
| 5,854,217 | 12/1998 | Maccecchini | 514/13 |

*Primary Examiner*—Keith D. MacMillan
*Attorney, Agent, or Firm*—Patrick D. Kelly

[57] ABSTRACT

Neuroprotective drugs are disclosed with at least 3 branches extending outwardly from a center atom or group, each branch having a guanidino group at its terminus. All branches preferably should be identical, and distributed around the center atom or group in a radial manner. Three branches can be bonded to a nitrogen atom, or four branches can be coupled to a carbon atom; other center groups include stable aromatic, cycloalkyl, heterocyclic, or bicyclic structures. Starting reagents are disclosed with a center atom or group, and with reactive groups (such as primary amines or hydroxyl groups) at the ends of short "spacer chains" bonded to the center atom or group. Reagents derived from arginine (an amino acid having a terminal guanidino group) can be bonded to these center components, using protective groups on the arginyl reagents to ensure desired final products with accessible guanidino groups at the ends of spacer chains. Alternately, guanylating agents can be used to directly convert primary amine groups at the ends of spacer chains, on starting reagents, into guanidino groups. These drugs can be injected intravenously into patients suffering from ischemic or hypoxic crises (stroke, cardiac arrest, loss of blood, suffocation, etc.), and can penetrate the blood-brain barrier and suppress the entry of calcium into CNS neurons via N-type and P/Q-type calcium channels, thereby reducing excitotoxic damage in the CNS. These drugs are also useful for suppressing other types of unwanted excessive neuronal activation, such as neuropathic pain.

25 Claims, 5 Drawing Sheets

NEUROPROTECTIVE POLY-GUANIDINO COMPOUNDS WHICH BLOCK PRESYNAPTIC N AND P/Q CALCIUM CHANNELS

RELATED APPLICATION

This application is a continuation-in-part of U.S. patent application Ser. No. 08/804,213, filed on Feb. 21, 1997.

BACKGROUND OF THE INVENTION

This invention relates to neurology and pharmacology, and to drugs for reducing brain damage in crisis situations such as stroke, cardiac arrest, drowning, or severe blood loss.

Neurons, especially in the central nervous system (CNS), can be severely damaged or killed by a condition called "excitotoxicity", which involves over-stimulation of neurons to a point where they begin dying. This condition arises during medical crises such as strokes, asphyxiation, carbon monoxide poisoning, cardiac arrest, internal hemorrhaging, severe blood loss, and various types of head injuries and other physical traumas. Certain types of poisons can also lead to excitotoxic brain damage. Seizures and convulsions due to epilepsy, head trauma, and various other causes also involve dangerous over-stimulation of neurons. Although relatively mild seizures are not presumed to cause neuronal death or permanent damage, severe seizures which cannot be halted by anti-seizure medications can cause permanent brain damage and neuronal death, due to excitotoxicity.

In addition, several types of progressive neurodegenerative diseases (such as Alzheimer's disease, Parkinson's disease, and amyotrophic lateral sclerosis) also are believed to involve excessive neurotransmitter activity as a component of the disease process.

These problems are severely aggravated by the inability of nerve cells to regenerate or repair themselves after injury. A child who suffers only a few minutes of perinatal asphyxia during birth may spend an entire lifetime horribly crippled by the injuries such damage can inflict. Many people who have suffered from strokes live the rest of their lives partially paralyzed, or unable to speak or remember major events in their lives due to permanent neuronal damage. Brain damage is an extremely serious medical problem which devastates individuals and their families, and inflicts enormous expense on insurance companies, government agencies, and others.

These costs are so high, largely because there currently are no effective drugs available for preventing or reducing brain damage during and after a crisis such as a stroke or cardiac arrest. Although stroke is the third leading cause of death in the United States, as of early 1997, not a single drug treatment has been approved by the U.S. Food and Drug Administration for preventing or reducing brain damage caused by stroke or any of the other causes of excitotoxic brain damage.

General Background on Neurons

The following is a very brief overview, intended mainly to direct the reader's attention to several cellular components and processes that are involved in this invention. For additional background information, a good single-volume textbook used at most medical schools is *Principles of Neural Science*, by Kandel & Schwartz (Elsevier Publishing, New York, 1996). Additional information is contained in G. Adelman's *Encyclopedia of Neuroscience* (Birkhauser Publishing, Boston), a multi-volume treatise, and in tens of thousands of scientific and medical articles, many of which are published in specialized journals such as *Brain and Brain Research*.

A neuron in the central nervous system (CNS) consists of a cell body, which contains the nucleus, and a strand-like projection called an axon, through which nerve impulses travel. The axon branches out into hundreds or even thousands of smaller fibrils, called synaptic processes. Each fibril terminates at a synaptic terminus, containing a small bulb-shaped area (a "bouton") which is bathed in extra-cellular synaptic fluid. The fluid fills the gap between the synaptic terminus (which is part of the "transmitting" neuron) and a receptor on a nearby "receiving" neuron.

Neurotransmitter molecules are stored at the end of each synaptic process, in synaptic boutons. One of the most important excitatory neurotransmitters in the mammalian CNS is glutamate, the ionized form of glutamic acid, an amino acid. Aspartate (the ionized form of aspartic acid, another amino acid) is also used by the brain as an excitatory neurotransmitter, but to a much lesser extent. Since glutamate and aspartate are amino acids, they are often called "excitatory amino acids", and glutamate receptors (discussed below) are sometimes called "excitatory amino acids receptors" (or EAA receptors).

When a nerve impulse reaches the end of a glutamate-containing axon, the glutamate molecules stored in the end of the axon are released into the extracellular synaptic fluid. These glutamate molecules temporarily bind to and react with glutamate receptors, which are proteins on the surface of the adjacent signal-receiving neuron (these proteins straddle the cell membrane, so that a portion of the membrane is exposed on the cell surface).

This brief binding reaction, between a glutamate molecule and a glutamate receptor, triggers a complex set of events in the signal-receiving neuron. The major steps in this reaction include: (1) opening of an ion channel associated with the receptor; (2) inflow of positively-charged calcium and sodium ions into the neuron, through the opened channel; (3) depolarization of the neuron, caused by the entry of charged calcium and sodium ions into the neuron.

This "depolarization" of a neuron by an incoming nerve signal (in the form of a glutamate molecule contacting a glutamate receptor on the neuron surface) is regarded as a triggering event, which takes the glutamate-triggered neuron into a brief state of hyperactivity. In order to be ready to receive an incoming nerve signal, neurons constantly try to maintain themselves in a polarized condition, i.e., in a condition where a relatively large electrical voltage potential (typically about −70 millivolts, mV) exists across the cell membrane, due to steep gradients of certain ions such as calcium. To maintain this polarization level, neurons pump calcium ions ($Ca^{++}$) and sodium ions ($Na^+$) outside the cell. This pumping action is so strong that the concentration of calcium ions outside a neuron, in the extracellular fluid that bathes a neuron, is roughly 10,000 times higher than the concentration inside the neuron.

In other words, the "resting" state of a neuron is a condition where the neuron is, in effect, sitting on top of an energy plateau. The neuron is ready to fire, in a manner comparable to a spring-loaded gun, where the spring is fully depressed and the mechanism is cocked, so that the gun is ready to fire a bullet as soon as the trigger is pressed. As soon as an incoming nerve signal arrives, the cell quickly depolarizes and triggers the sequence of events that lead to release of its own neurotransmitters. In effect, when this depolarization/firing occurs, the neuron comes down off of its high-energy, ready-to-fire plateau. Within a few milliseconds after that, the neuron begins working (and expending energy) to pump out calcium and sodium ions again, to regain its polarized resting state, so that it will be ready to receive the next nerve impulse.

There are also other ion gradients that exist across neuronal membranes, due to both active pumping and passive diffusion. Potassium ions (K$^+$) are pumped inside neurons, but that pumping system is relatively weak. Chloride ions (Cl$^-$) are driven out of a neuron, but this is due to the electronegativity of the fluid inside a resting cell, and is not believed to be due to an ion-specific pump.

The depolarizing flow of calcium and sodium ions into a neuron also causes other cellular responses at other locations (often called "downstream" locations) on the neuron. If the triggering event is sufficiently strong to overcome the effects of various inhibitory neurotransmitters (such as dopamine, serotonin, or GABA), then the depolarizing event will cause the neuron to release some of its own glutamate molecules at one or more downstream synaptic terminals, thereby passing the nerve signal on to other neurons, which then undergo similar depolarizing activation events as they pass on the nerve signal(s) to still other neurons.

Glutamate neurotransmitter molecules do not permanently bond to glutamate receptors at a synaptic junction. Instead, the glutamate molecules quickly disengage from the glutamate receptors and return to the synaptic fluid. Under normal and healthy conditions, the glutamate molecules which have been released by the receptors are rapidly pumped back into the neurons (or into glial cells, which effectively act as support cells inside the brain), by a glutamate transport system, which requires energy to carry out its pumping actions. This prevents glutamate from accumulating in the synaptic gaps between neurons, where it might cause excess stimulation of signal-receiving neurons.

However, in crisis conditions such as stroke or cardiac arrest, the transport system which normally removes the glutamate from the synaptic fluid runs out of energy, and can no longer function properly. When this happens, excess glutamate begins to accumulate in the synaptic gaps between neurons. This can quickly lead to a toxic condition, where the presence of lingering glutamate in the synaptic junctions causes severe and possibly continuous overstimulation (excitation) of the glutamate receptors.

This type of uncontrolled activation by glutamate is a key factor in "excitotoxicity" in the brain. It can lead to rapid and dangerous cellular deregulation, and it can severely aggravate and expand the amount of permanent brain damage that is suffered by a victim. By way of illustration, in many stroke victims, the central area of damaged brain tissue (which died because it lost its blood supply) is often surrounded and accompanied by a substantial "penumbra" of dead or dying neurons which were not directly affected by the loss of blood supply. Even though they were not directly affected by a cutoff of their blood supply, the dead or dying neurons in this penumbra region were, in effect, dragged into a toxic cascade, in which dangerously overstimulated neurons began releasing uncontrollable amounts of glutamate. Under excitotoxic conditions, the same glutamate molecules which play an essential role as neurotransmitters, in a healthy brain, can become deadly toxins. When this condition occurs, the glutamate molecules begin to unleash neurotoxic processes that can quickly lead to the deaths of penumbral neurons that are outside the region of brain tissue that was directly injured by a loss of blood flow.

Ischemia, Hypoxia, and Neuron Damage

The requirement that neurons must very rapidly pump out calcium and sodium ions to regain a "ready to fire" status within a few milliseconds after an activation spike leads to a number of biochemical factors that help explain how and why the brain and spinal cord can be so rapidly and badly damaged, during and after an ischemic or hypoxic crisis.

The conditions which most commonly cause brain damage are referred to by physicians and researchers as ischemia (which refers to lack of adequate blood flow) and hypoxia (which refers to inadequate oxygen supply). Ischemia occurs in the brain during a stroke, cardiac arrest, severe blood loss due to injury or internal hemorrhage, and other similar conditions that disrupt normal blood flow. It also occurs after a head trauma that causes "edema" (fluid accumulation which leads to swelling of soft tissue) inside the brain, since the pressure caused by edema presses against and flattens the arteries and veins inside the brain, thereby reducing their ability to carry blood through the brain.

Hypoxia also can be caused in various ways. It is a direct result of ischemia; whenever blood supply is cut off, oxygen supply is also cut off as a direct result. However, hypoxia can occurs in various other conditions, even if blood flow remains unaltered; examples include carbon monoxide poisoning, drowning, suffocation, and other forms of asphyxia.

Hypoglycemia (an inadequate supply of glucose in the blood, which can occur due to conditions such as malnutrition, or an overdose of insulin in a diabetic) is less common, but it is also a substantial medical problem. All discussion herein relating to the use of calcium channel blockers to prevent or reduce excitotoxic brain damage is also applicable to preventing or reducing brain damage caused by hypoglycemia.

Because of certain physiological factors (e.g., neurons have no reserve supplies of glucose or oxygen), the brain and spinal cord are much more vulnerable to ischemic or hypoxic damage than any other organ, and permanent brain damage (including neuronal death) begins to occur within a few minutes. Because of their crucial roles in the body, damage to the brain or spinal cord can be quickly lethal, or can inflict permanent crippling damage and utter devastation to a victim's life.

Neurologists and other researchers have spent billions of dollars trying to develop drugs that can prevent or reduce ischemic or hypoxic damage to the brain and spinal cord. Although a number of approaches appear to hold promise for the future, the sad and tragic fact is that, as of early 1998, not a single type of drug which can effectively reduce or prevent excitotoxic brain damage due to stroke, cardiac arrest, asphyxiation, blood loss, or similar crises, is available to people who need such help; the only arguable exception is clot-dissolving drugs, such as streptokinase and tissue plasminogen activator, which can help dissolve blood clots, but which do not otherwise block or reduce the processes involved in glutamate excitotoxicity.

A great deal of neurological research on efforts to reduce ischemic/hypoxic brain damage has focused on synaptic receptors, especially glutamate receptors, because of the role glutamate accumulation plays in excitotoxicity. One of the primary theories behind this research is that if drugs can be used to prevent excessively accumulating glutamate from contacting glutamate receptors in the synaptic junctions between neurons, then the signal-receiving neurons will not be so vulnerable to toxic over-stimulation.

However, since glutamate is an essential neurotransmitter, global blockade of glutamate receptors can impose severe disruptions on proper and necessary neurological functioning, and can cause dangerous and potentially brain-damaging or even lethal side effects. Researchers studying drugs that can selectively block certain subclasses of glutamate receptors (these subclasses include NMDA receptors, kainic acid receptors, and AMPA receptors) have been claiming for years that these drugs can reduce brain damage in ischemia or hypoxia. However, most of those drugs have toxic side effects, and despite the claims of the researchers, no such drugs are available for public use—not even for critically ill patients who are dying of massive strokes or cardiac arrest.

Accordingly, attention by some researchers has recently turned toward various other avenues, including methods of reducing ion flow through the calcium channels that allow calcium ions to enter neurons during a depolarizing (activating) event. This field of research is discussed below.

Calcium Channels

Detailed information on neuronal calcium channels (and on various drugs that can selectively block calcium entry through different classes of calcium channels) is contained in articles such as Bertolino and Llinas 1992, Olivera et al 1994, Dunlap et al 1995, and Wheeler et al 1996.

Briefly, neurons possess at least four (and possibly more) types of calcium channels, located in their plasma membranes. The three classes which were known by the mid-1980's are called N, L, and T channels (Nowycky et al 1985). More recently, a fourth class called P channels has been widely recognized. Other classes, tentatively called the O, Q, and R channels, have also been suggested, but they are not yet widely agreed upon and identified consistently by all neuroscientists.

Based on various published reports and on original research by the Inventors herein, it is believed that P-type and Q-type calcium channels belong to a "P/Q" family. They are distinct from each other in certain ways, but they share a relatively high degree of homology and cross-reactivity (also called cross-affinity). Because of their relatively high levels of homology and cross-reactivity, P-type and Q-type channels respond similarly to various types of drugs, apparently including the radial poly-guanidino drugs that are the subject matter of this invention. Accordingly, references herein to "P/Q channels" are deemed to include references to either or both types of channels. Similarly, phrases such as "poly-guanidino drugs which can block P/Q channels" are intended to apply to radial poly-guanidino drugs as described herein which can block either P-type channels, or Q-type channels. To the best of the Applicants' knowledge and belief, all of the poly-guanidino compounds tested to date in tissue culture or in vivo tests (described below) block both P-type and Q-type calcium channels, as well as N-type calcium channels.

The four main classes of calcium channels (L, N, T, and P) can be distinguished from each other, in cell culture experiments, by the fact that certain drugs bind to the different classes of calcium channels with differing affinities. Certain dihydropyridine drugs (such as flunarizine, nicardipine, and nifedipine) bind to L-type channels, but not to T or N channels. Other fast-acting poisons called omega conotoxins (used in nature by marine snails of the genus Conus, to catch and paralyze fish) bind very tightly to N-channels, less tightly to L-channels, and even less tightly to T-channels (Kasai et al 1987). Certain types of spider toxins called agatoxins bind tightly to P channels (and possibly to Q-type channels as well).

All four of these classes of $Ca^{++}$ channels exist on the surfaces of neurons, but not in the same locations. In neurons, L-type and T-type channels are located on the main body of a neuron, and on a neuron's dendrites (which are finger-like fibrils that carry arriving nerve impulses from a receptor-bearing synapse toward the main body of the neuron). Accordingly, both L and T channels can be regarded as post-synaptic channels; they are involved in how a neuron responds to a nerve impulse, after the impulse has arrived at an impulse-receiving synapse.

By contrast, N-type and P-type calcium channels are positioned "downstream" from the cell nucleus; they are positioned between the cell nucleus and a different set of synapses that will pass on nerve signals to other neurons. For this reason, N-type and P-type calcium channels are often called pre-synaptic calcium channels.

It is generally agreed among most researchers that calcium entry through N or P/Q channels is a necessary step in a series of neuronal actions that enable the release of glutamate (and, to a lesser extent, aspartate) from synaptic boutons as a neuron transmits a nerve signal to other neurons. Accordingly, conotoxins (from marine snails) or agatoxins (from spiders) which can selectively block the entry of calcium into neurons through N-type or P-type calcium channels can prevent the activated neurons from releasing glutamate. This effectively blocks the drug-treated neurons from transmitting the nerve signal to other neurons.

Drugs Disclosed in the Prior Art

The discoveries above, relating to pre-synaptic N and P/Q channels, have led to various efforts to develop drugs (modelled after the conotoxins or agatoxins) that can suppress glutamate release by excited neurons. Efforts to create peptide segments modelled after snail toxins, to suppress calcium entry via N-channels, are described in Patent Cooperation Treaty (PCT), number WO-91/07980 (invented by Miljanich et al, assigned to Neurex Corporation of Menlo Park, Calif.). Efforts to suppress calcium entry via P-channels, involving both peptide and non-peptide molecules modelled after spider toxins, are described in U.S. Pat. Nos. 4,925,664 (Jackson et al 1990), 4,950,739 (Cherksey et al 1990), 5,122,596 (Phillips et al 1992), and in numerous items of prior art cited therein.

Most of the spider toxins which can block P-channels contain large numbers of amine groups, in relatively small molecules. That realization led to the creation of various types of polyamines which assertedly can block calcium entry through P-channels. Such polyamines are described in, for example, U.S. Pat. Nos. 5,037,846 (Saccomano et al 1991); 5,227,397 (Saccomano et al 1993); and 5,242,947 (Cherksey et al 1993), and in various articles cited therein.

Various other efforts also have been made by other research teams to develop other drugs containing multiple amine groups, for neuroprotective purposes. In particular, Goldin et al (at Cambridge NeuroSciences) and Weber and Keana (at the University of Oregon and Oregon Health Sciences University) have each developed various amine compounds derived from guanidine, having the general structure:

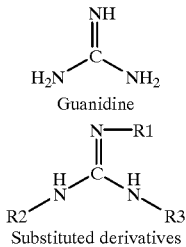

where the various R groups are selected from any number of organic moieties listed in various U.S. patents. The Goldin et al/Cambridge NeuroScience patents involving guanidine derivatives include U.S. Pat. Nos. 5,403,861 (April 1995); 5,438,130 (August 1995); 5,614,630 (March 1997); 5,622, 968 (April 1997); 5,637,623 (June 1997); 5,652,269 (July 1997); 5,670,519 (September 1997); 5,672,608 (September 1997); 5,677,348 (October 1997); 5,681,861 (October 1997); and 5,686,495 (November 1997). Similar patents which involve guanidine derivatives and which list Weber and Keana as co-inventors include 4,709,094 (November 1987); 4,906,779 (March 1990); 5,093,525 (March 1992); 5,190,976 (March 1993); 5,262,568 (November 1993); 5,308,869 (May 1994); 5,312,840 (May 1994); 5,478,863 (December 1995); 5,502,255 (March 1996); 5,552,443 (September 1996); 5,559,154 (September 1996); 5,574,070 (November 1996); 5,604,228 (February 1997); and 5,637,622 (June 1997). As should be apparent from the dates, not all of these patents are prior art against the current invention, which was originally disclosed in an application filed in February 1996. However, as mentioned below, none of these patents are believed to involve arginine residues, and they do not involve radial branches that are evenly distributed around a central atom such as a tertiary amine or a benzene ring.

Weber, Keana, et al also have developed various bicyclic compounds derived from quinoline or quinoxaline-diones, as shown below:

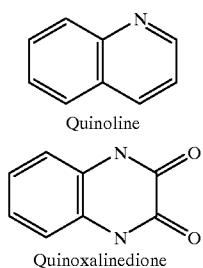

Quinoline

Quinoxalinedione

Such compounds are discussed in, for example, U.S. Pat. Nos. 5,475,007 (December 1995); 5,514,680 (May 1996); 5,597,922 (January 1997); 5,620,978 and 5,620,979 (April 1997); 5,622,952 (April 1997); 5,622,965 (April 1997); 5,631,373 (May 1997); and 5,652,368 (July 1997).

Another nitrogen-containing class of compounds that were identified as calcium channel blockers is described in U.S. Pat. No. 5,312,928 (Goldin et al, Cambridge NeuroScience, May 1994). These compounds are relatively complex molecules, having a bicyclic structure coupled via an amidine linkage to a linear nitrogen-containing structure.

To the best of the Applicant's knowledge and belief, none of the compounds listed in the above-cited US patents by Goldin et al or by Weber, Keana et al contain arginine residues. The only compounds known to the Applicant company which contain arginine residues, and which have been asserted to offer neuroprotective benefits by suppressing activity at calcium channels, are peptide (proteinous) molecules, in which multiple amino acids are coupled to each other in a linear chain via conventional peptide bonds (as used by cells to make proteins from amino acids). However, peptide drugs tend to cause substantial problems and suffer from other limitations when administered to humans, for various reasons including: (1) peptide drugs are readily broken down by the digestive system, if administered orally; and (2) foreign peptides can cause major problems by provoking immune rejection responses, if injected into a patient. Accordingly, most peptide drugs are strongly disfavored, if other non-peptide drugs can be identified and developed which have comparable useful activity without having a peptide structure.

Additional types of nitrogen-containing compounds are disclosed in U.S. Pat. No. 5,599,984 (Bianchi et al, Picower Institute, February 1997). Some of the compounds disclosed herein have radial structures, using a center nitrogen atom (such as compounds 31 and 34–36, in FIGS. 7G and 7H of the '984 patent) or a center benzene ring (such as compounds 28, 32, and 33, in FIGS. 7F and 7G). However, none of the compounds disclosed in the '984 patent used arginine residues. In addition, those compounds were not disclosed as being neuroprotective; instead, there were identified as being anti-inflammatory agents, and agents useful for suppressing arginine uptake, to help fight arginine-dependent tumors and infections.

Accordingly, despite all of the above-cited work (as well as decades of other research by thousands of other skilled neurological researchers), there are not yet available, to victims of stroke, cardiac arrest, asphyxiation, head trauma, or other medical crises that lead to ischemia or hypoxia in the brain, any compounds which can safely and effectively prevent or reduce excitotoxic brain damage. To the best of the Applicant's knowledge and belief, the compounds disclosed above all suffer from one or more limitations, such as cytotoxic side effects, low ability to permeate blood-brain barriers, difficulty in synthesis or purification, etc.

In addition, based on research carried out by the Applicant herein (Cypros Pharmaceutical Corporation), it appears that suppression of calcium entry at both N-type and P-type (and possibly Q-type) calcium channels may be more beneficial than selective blockade of only one class of pre-synaptic channels, in preventing or reducing excitotoxic damage to neurons.

Furthermore, the compounds disclosed herein have been shown to perform quite well in protecting brain tissue against ischemic or hypoxic damage, both in tissue culture tests, and in in vivo tests on live adult mammalian animals. In the in vivo tests on intact animals, these compounds penetrate blood-brain barriers and effectively protect the brain tissue against genuine ischemia, rather than merely against simulated ischemia, as used in cell culture tests.

Accordingly, one object of the subject invention is to disclose new compounds which can suppress calcium ion entry into neuron via pre-synaptic N-type and P/Q-type calcium channels.

Another object of the invention is to disclose new compounds which can suppress pre-synaptic calcium entry into neurons more effectively, by blocking both N-type and P/Q-type calcium channels rather than blocking only one class of pre-synaptic calcium channel.

Another object of this invention is to disclose drugs and methods which can help prevent or reduce excitotoxic damage to neurons, both in the CNS and in the peripheral nervous system.

Another object of this invention is to disclose improved methods of synthesizing drugs that can offer neuroprotective benefits during and after ischemic and hypoxic crises, by suppressing calcium ion entry into neurons through pre-synaptic calcium channels.

Another object of this invention is to disclose a new class of drugs useful for suppressing certain types of unwanted excessive neuronal activation, including neuropathic pain.

These and other objects of the invention will become more apparent through the following summary, drawings, and description of the preferred embodiments.

SUMMARY OF THE INVENTION

This invention discloses branched poly-guanidino compounds having at least 3 branches extending outwardly from a center atom or group, with each branch containing a guanidino group at its terminal end. All such branches can be identical to each other, to facilitate easier synthesis, and preferably should be bonded to the center atom or group in an evenly-distributed "radial" arrangement. For example, three such branches can extend outwardly and radially from a center nitrogen atom or benzene ring; alternately, four such branches can extend outwardly from a center carbon atom, benzene ring, or cycloalkane or heterocyclic center groups.

To synthesize these compounds, starting reagents such as tris(2-aminoethyl)amine or tris(3-aminopropyl)amine can provide reactive groups (such as primary amine groups) positioned at the ends of "spacer chains" (having, for example, 2 to 4 carbon atoms) bonded to a center atom or group. Reagents derived from arginine (a naturally occurring amino acid which contains, as its side group, a guanidino group at the end of a spacer chain) can be chemically bonded to the reactive groups at the ends of the spacer chains. Protective groups at selected locations on the arginyl reagents can prevent those reagents from bonding to the center reagent in undesired orientations. After the arginine coupling reactions have been completed, the protective groups can be removed to provide an accessible guanidino group at the terminus of each arginyl branch. These guanidino groups, which effectively have been positioned at the ends of spacer chains to increase their accessibility, can contact and interact with both N-type and P/Q-type calcium channels, on neuronal surfaces.

These poly-guanidino drugs can be injected intravenously into patients suffering from medical crises that involve ischemia (inadequate blood flow) and/or hypoxia (inadequate oxygen supply) in the brain. After these poly-guanidino drugs enter the bloodstream, they can penetrate the blood-brain barrier and suppress the entry of calcium ions into neurons via N-type as well as P/Q-type calcium channels. By suppressing calcium entry into neurons via those channels, these drugs can help protect against excito-toxic damage to CNS neurons.

The compounds of interest herein exclude polypeptides, which suffer from various limitations when used as injectable drugs. The compounds of interest also are limited to non-polymeric molecules, preferably having molecular weights of less than about 1500 daltons. They must be pharmacologically acceptable in humans suffering from ischemic crises, and they must be able to penetrate blood-brain barriers and reduce neuronal damage after intravenous injection when tested using animal models of brain ischemia. Tests of such radial polyarginine compounds as disclosed herein, using in vitro as well as in vivo assays, indicate that they are effective and useful as neuroprotective drugs. In addition, these compounds are also anticipated to be useful in treating certain other types of unwanted excessive neuronal activation, such as neuropathic pain.

DESCRIPTION OF THE PREFERRED EMBODIMENTS

Figure 1:
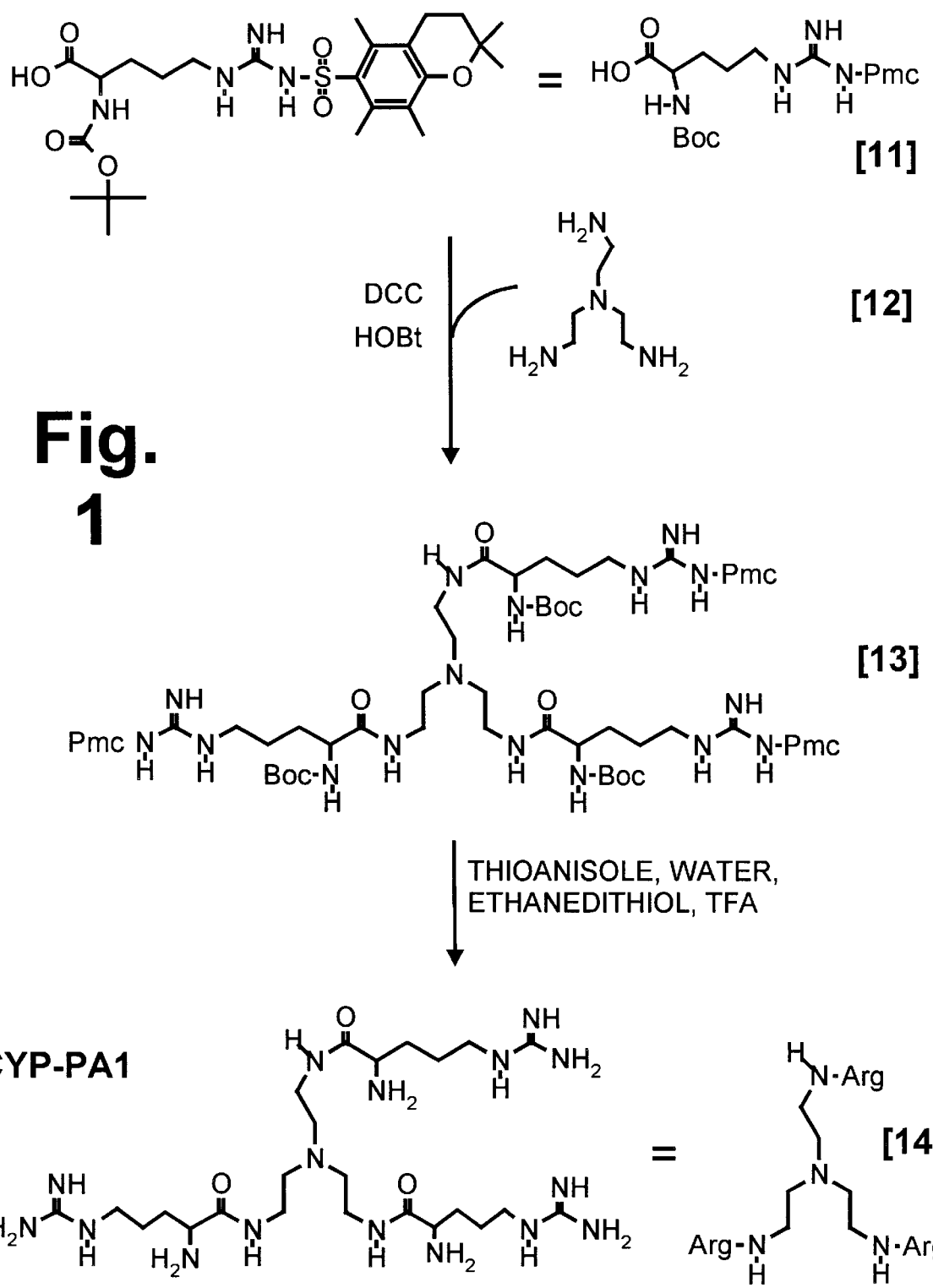
FIG. 1 depicts the synthesis of compound CYP-PA1, with three branches in a radial configuration coupled to a center nitrogen atom, with an arginine residue bonded to each branch through a short spacer chain, in a configuration which generates accessible primary amine groups at the ends of all three branches.

Referring to the drawings, FIG. 1 depicts the synthesis and structure of a compound designated as CYP-PA1, with a single nitrogen atom (a tertiary amine) at the center, and with three branches extending radially from the center nitrogen. Each branch has an arginine residue, bonded to the branch in a configuration that maximizes the number of "accessible" amino groups that can contact and react with N-type and/or P/Q-type calcium channels on neurons.

In the compound designation CYP-PA1, "CYP" refers to the assignee company (Cypros Pharmaceutical Corporation, of Carlsbad, Calif.) and PA1 refers to a certain polyarginine compound in a numbered series. This same compound can also be referred to by the chemical name tris(arginyl-2-aminoethyl)amine; the "tris" prefix indicates that three arginylaminoethyl branches are coupled to the center nitrogen (amino) atom.

As used herein, the term "radial" is used to refer to a compound having at least three branches which have equivalent sizes and structures, and which are evenly distributed around a center atom or group, in a manner comparable to the spokes of a wheel. The compounds shown at the bottoms of FIGS. 1 through 4 are all radial compounds which satisfy these criteria. Similarly, four identical branches extending outwardly from a six-membered ring (such as benzene, cyclohexane, or a heterocyclic ring) would be regarded as "radial" if they are evenly distributed around the ring (i.e., if the two "unoccupied" carbon atoms are on opposite sides of the ring). For example, if the #1, #2, #4, and #5 carbon atoms of a six-membered ring provide the attachment points for branches, while the #3 and #6 carbon atoms are not attachment points for branches, the resulting compound would be regarded as a radial compound. Radial compounds can also be regarded as being symmetric about a point; if a drawing of a radial compound having 3 branches is rotated 120°, it will look the same, while if a radial compound having 4 branches is rotated 90°, it will look the same. Similarly, if a compound with 4 radial branches on a benzene or cyclohexane ring is rotated 180°, it will look the same.

By contrast, compounds such as the substituted guanidine derivatives disclosed in the patents of Goldin et al or in the guanidine-related patents of Weber and Keana are not radial compounds, and do not have identical branches, since the center guanidine component of those compounds provides a double-bonded branch having a different structure than the single-bonded branches.

In general, a compound wherein all of the branches are identical to each other (especially if they are positioned in a radial arrangement around the center atom or group) provides various advantages in simplifying the synthesis and purification reactions, when compared to the requirements of using different reactions to create different types of branches on a non-radial compound with different types of branches.

As used herein, the "center component" of a neuroprotective poly-guanidino as disclosed herein refers to an atom or a stable molecular group which can provide a chemically stable attachment point for at least three branches, which are directly bonded to the center component (rather than sub-branches, bonded to attachment points in other branches). Preferred types of "center components" for use as described herein include: (1) a nitrogen atom, which can serve as an attachment point for three identical branches; a carbon atom, which can serve as an attachment point for four identical branches; various stable cyclic constituents, including aromatic compounds such as benzene and its derivatives such as phenol or toluene; stable cycloalkyl compounds such as cyclohexane and possibly cyclopentane or cycloheptane; and stable single-ring heterocyclic compounds, such as pyridine, pyrrole, furan, imidazole, thiophene, thiazole, and oxazole. Various stable bi-cyclic compounds (such as naphthalene, quinoline, isoquinoline, indole, benzofuran, and benzothiophene) also provide good candidates for evaluation as center components in neuroprotective polyguanidino compounds as disclosed herein.

Various derivatives of these cycloalkane and heterocyclic compounds which offer good starting reagents are commercially available, or can be synthesized using known techniques. As one example, a reagent known as "Kemp's tri-acid" is available, which is a cyclohexane ring which has a methyl group and a carboxylic acid group bonded to each of the #1, #3, and #5 carbon atoms on a saturated (non-aromatic) 6-carbon ring. Each of the three carboxylic acid groups on this ring can be converted into a primary amine group, by means such as the steps shown at the top of FIG. 5, then each of the three primary amine groups can be converted into either (i) an arginine residue, using steps such as shown in FIGS. 1–4, or (ii) a guanidino group, using a guanylating agent such as shown on the right side of FIG. 5. Either approach would provide a tri-guanidino compound having a guanidino group at the end of each of three spacer chains, evenly distributed in a radial manner around a cyclohexane ring.

As used herein, the term "branch" (and "guanidino branch", which is used interchangeably herein with "branch") refers to a portion of a molecule which (a) extends outwardly from a center component of the molecule, (b) contains at least five atoms, other than hydrogen; and (c) contains a guanidino group at its terminus, as shown in the various figures, and as occurs naturally in the amino acid arginine. Viewed from another perspective, a "branch" or "guanidino branch" is also defined herein as guanidino group at the end of a "spacer chain", which preferably should contain at least 1 and up to about 7 carbon atoms. A "spacer chain" allows the guanidino group at the end of the branch to have greater accessibility and lower levels of steric hindrance, comparable to a hand at the end of a long and flexible arm, rather than at the end of a short, stubby arm. This gives the terminal guanidino groups greater ability to contact and interact with N-type and P/Q-type calcium channels on the surfaces of neurons, which in turn gives the guanidino groups at the ends of the branches greater neuroprotective efficacy, since they can more effectively inhibit calcium ion entry into activated neurons through those calcium channels.

The synthesis of CYP-PA1 is described in detail in Example 1, and in corresponding FIG. 1. In all of the examples, bracketed numbers are used in the text to indicate corresponding numbered compounds in the figures. To minimize complexity and confusion in the text and figures, protective groups (such as butyloxycarbonyl or pentamethylchroman groups) are shown once in the figures, and subsequently indicated by their acronyms (such as Boc and Pmc, respectively). These protective groups are used to prevent premature reactions during synthesis, and to ensure that arginine residues are coupled to the tertiary amine starting reagent in the desired configuration. When the protective groups are no longer needed to prevent undesired reactions, they are removed, usually by means of an acid (such as trifluoroacetic acid, TFA) which hydrolyzes and removes the protective groups. This "deprotection" step usually occurs at or near the end of a synthetic pathway, and other compounds (such as thioanisole and ethanedithiol) may also be used, to prevent unwanted oxidative and other reactions.

It should be noted that most arginine reagents used in the syntheses disclosed herein contained two different types of protective groups. For example, the starting reagent shown at the top of FIG. 1 used Boc as a protective group for one of the primary amine groups (the "peptide" amine group, which normally becomes part of the peptide bond when arginine is added to a peptide chain), and Pmc as the other protective group for the "side chain" primary amine group. This allows for greater flexibility and control during synthesis. The Boc protective group can be removed relatively quickly and easily, by treatment with an acid such as trifluoroacetic acid (TFA) for about 20 minutes. By contrast, other protective groups such as Pmc or Mtr require a much more prolonged reaction to remove them, such as a 4-hour treatment using TFA to remove the Pmc group in Example 1 and FIG. 1, and a 14-hour treatment using TFA to remove the Mtr group in Example 3 and FIG. 3.

Arginine reagents that contain two different protective groups are commercially available, since such reagents offer a method of working with arginine that can be adapted to any of numerous chemical needs. The arginine reagent which contained both a Boc group (on the peptide amine) and a Pmc group (on the side-chain amine) was purchased from Bachem Chemical Company, located in King of Prussia, Pa. The arginine reagent which contained a Boc group (peptide amine) and an Mtr group (side-chain amine) was purchased from Novabiochem, located in San Diego, Calif.

Figure 2:
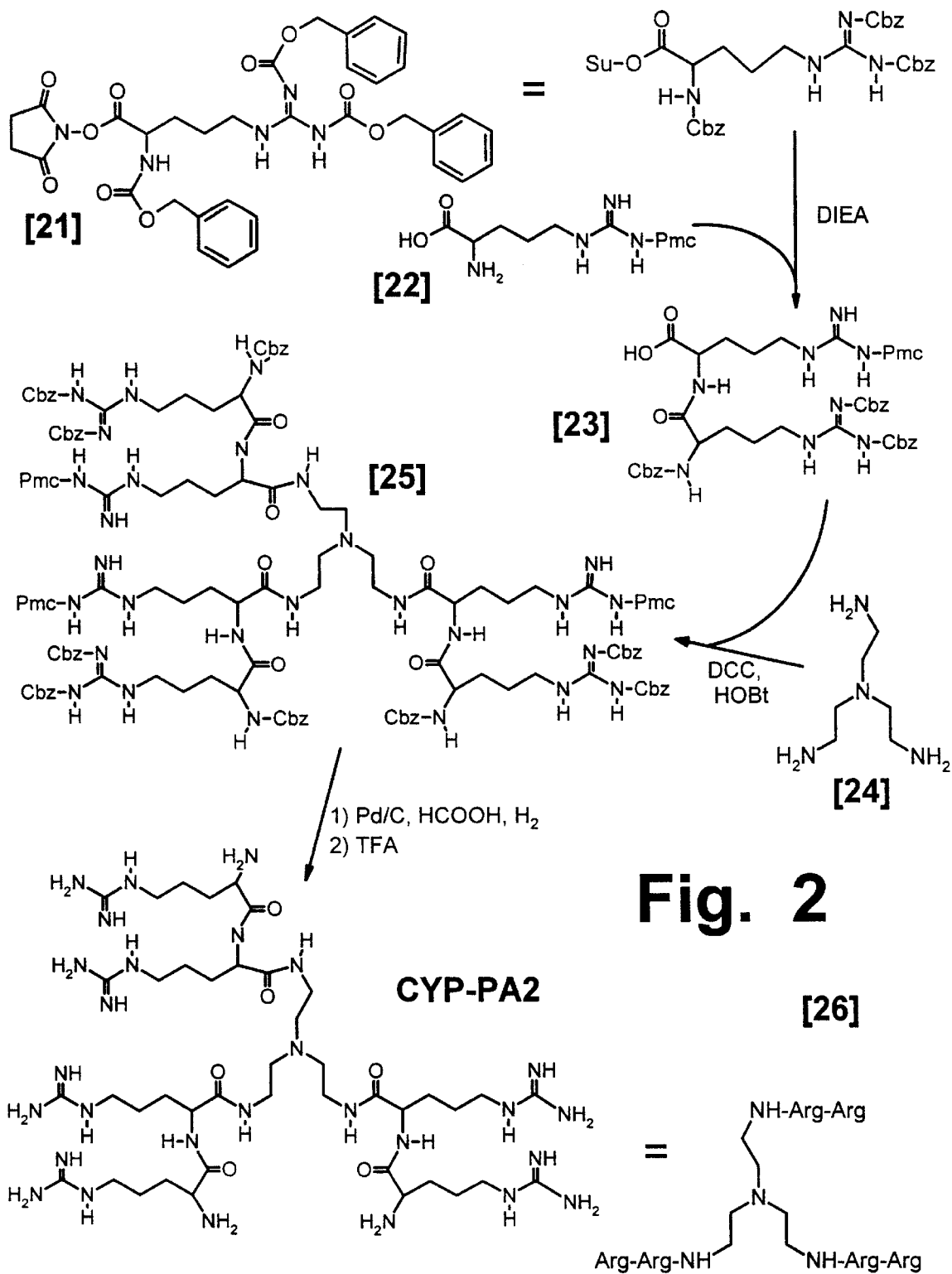
FIG. 2 depicts the synthesis of compound CYP-PA2, with three branches in a radial configuration, with two arginine residues in each branch for a total of six arginine residues.

Example 2 and FIG. 2 describe the synthesis of a di-arginyl compound, designated as CYP-PA2. Since this compound has three arms, the term "di-arginyl" indicates that two arginine residues are coupled to each arm. This provides a total of six arginine residues, in the final compound.

Example 2A (which has no corresponding figure) describes an "unsaturated" by-product which was isolated as an impurity during purification of CYP-PA2. In this unsaturated compound, designated as CYP-PA2X, it was found that the di-arginyl groups had been bonded to only two of the three arms. It was shown to be not as potent as the fully-saturated corresponding compound, in in vitro tests, and it was not tested in any in vivo tests.

Figure 3:
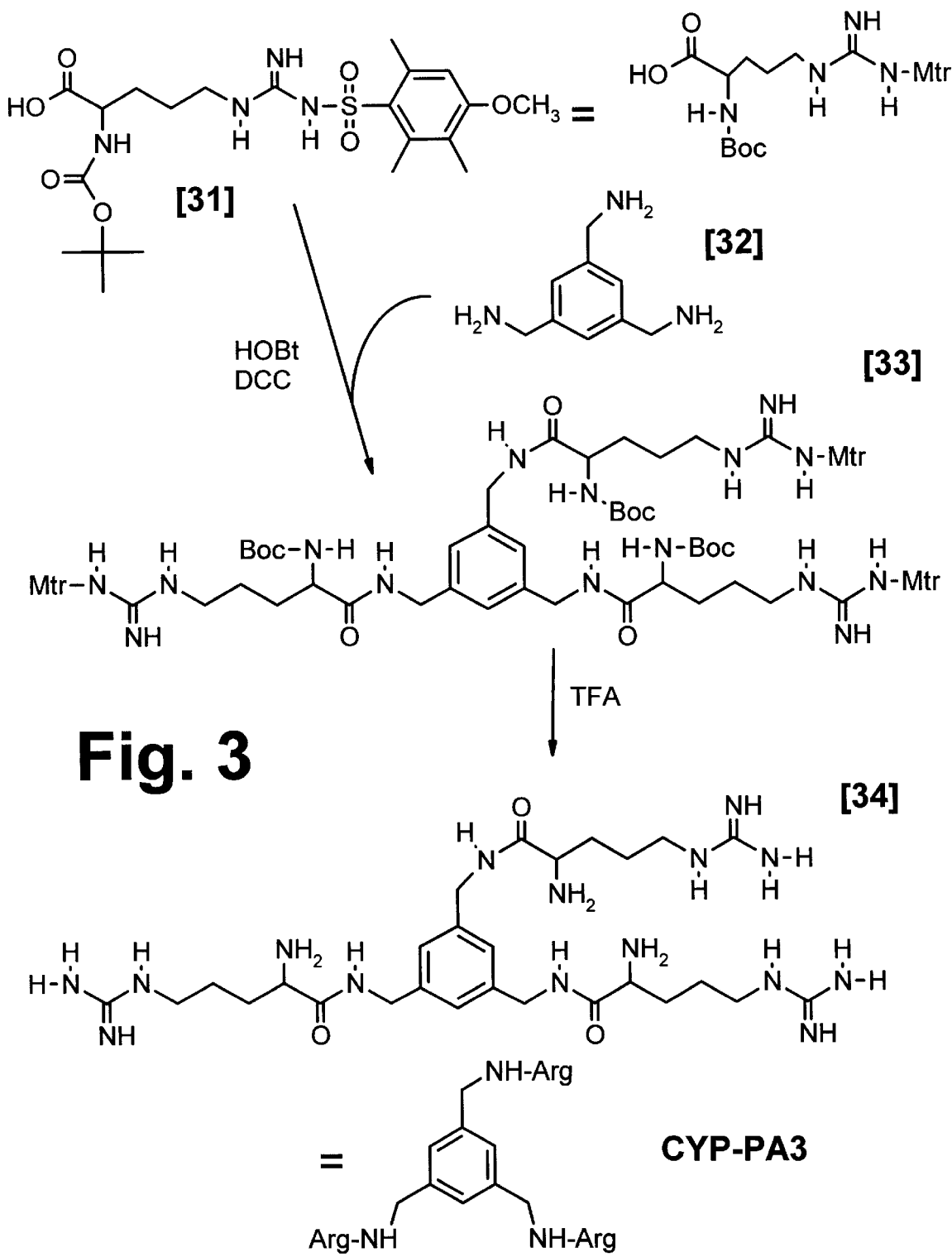
FIG. 3 depicts the synthesis of compound CYP-PA3, with three branches coupled to a center benzene ring, with a single arginine residue in each branch.

Example 3 and FIG. 3 describe the synthesis of a compound with three radial branches containing arginine residues, with the arms attached to a benzene ring in the center. This compound, designated as CYP-PA3 in the Tables, contained a single arginine residue on each arm.

Figure 4:
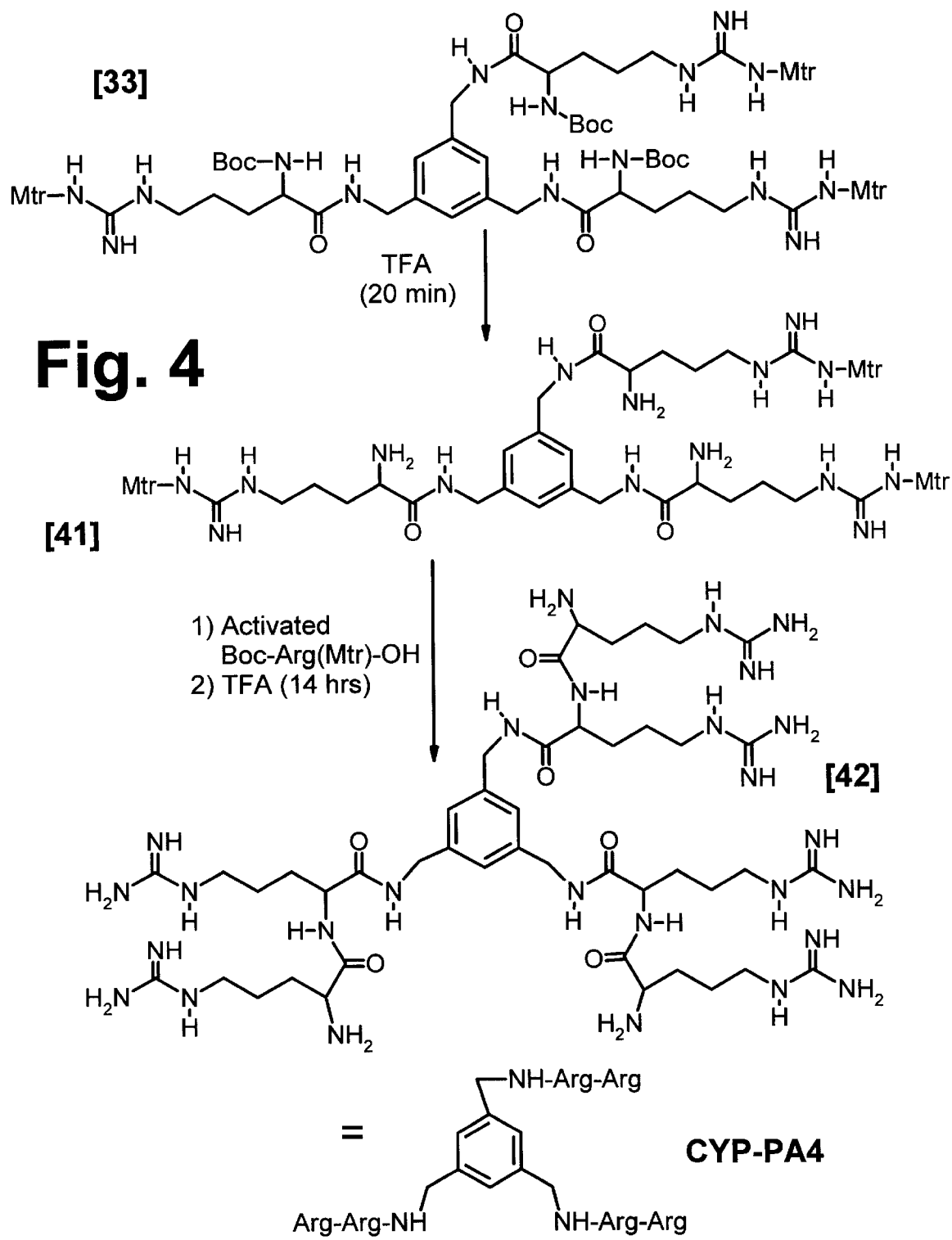
FIG. 4 depicts the synthesis of compound CYP-PA4, with three branches coupled to a center benzene ring, with two arginine residues in each branch.

Example 4 and FIG. 4 describe the synthesis of a compound with three radial branches containing two arginine residues in each branch, attached to a benzene ring in the center. This compound, designated as CYP-PA4, is a tris (diarginyl) compound.

Example 5 discloses a general method for using any of several known "guanylating" agents, such as 1H-pyrazole-1-carboxamidine; 2-methyl-2-thiopseudourea; O-methyl-isourea; formamidinesulfonic acid; 3,5-dimethylpyrazole-1-carboxamidine nitrate; N-[bis(methylthio)-methylene]-p- toluene-sulfonamide; and cyanamide) to convert a primary amine group into a guanidino group. An example of such a reaction is illustrated in FIG. 5, in the final step of the synthesis of CYP-PA/C4G.

Figure 5:
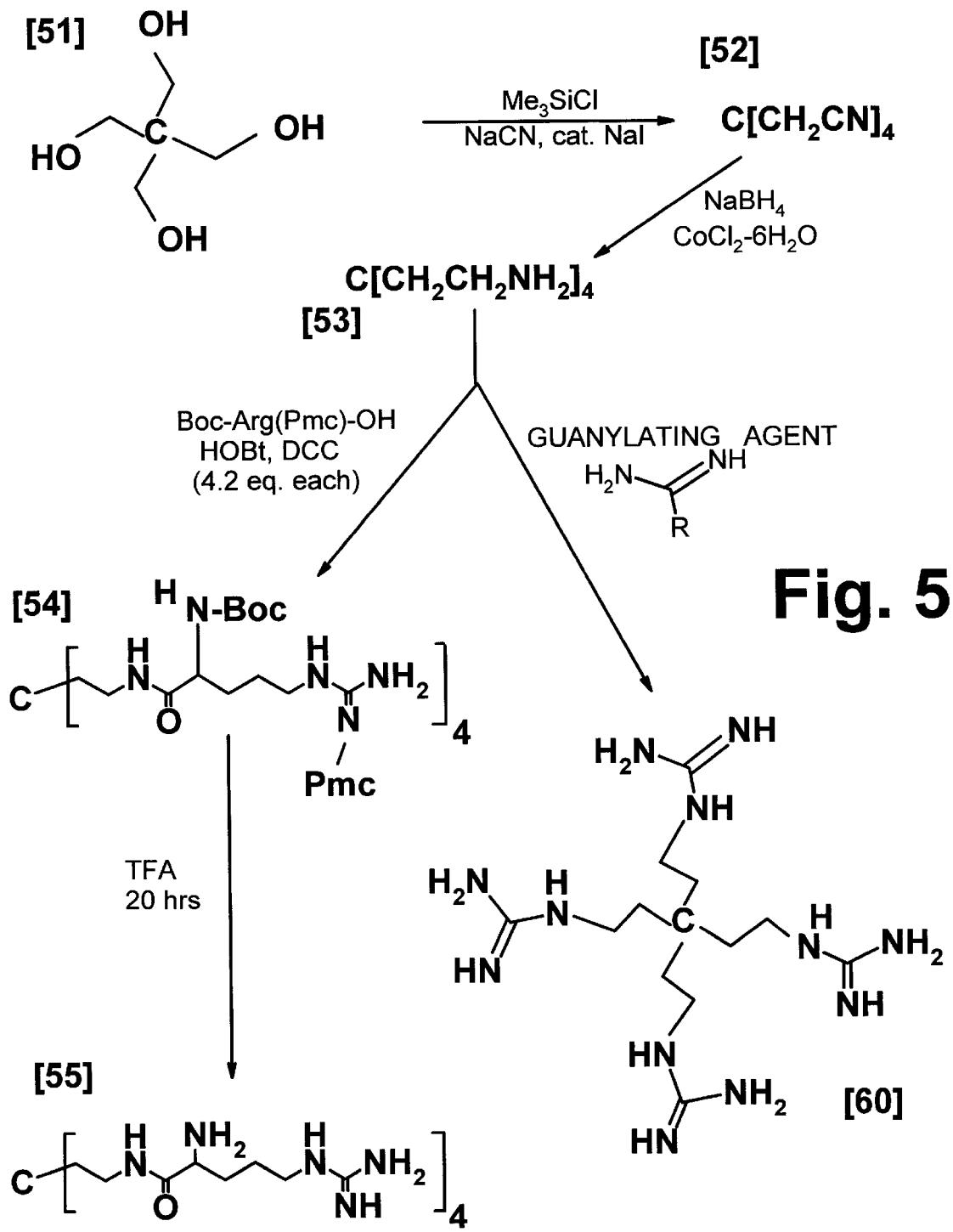
FIG. 5 depicts the synthesis of CYP-PA/C4A and CYP-PA/C4G, with four branches coupled to a center carbon atom. CYP-C4A has an arginine group in each branch, while CYP-C4G is a somewhat simpler compound with a guanidino group at the end of each branch.

Example 6, and FIG. 5, disclose a general synthetic method for creating tetra-arginyl or tetra-guanidino compounds, having four branches bonded to a center carbon atom. Due to fact that these compounds have multiple amine groups at the end of a chain, in the same types of guanidino formations that also are believed to play a key role in providing the neuroprotective activities of the branched tri-arginine and hexa-arginine compounds, these tetra-arginyl and tetra-guanidino compounds are believed to have similar neuroprotective activities due to the their ability to suppress calcium ion entry through the N-type and P/Q type neuronal calcium channels. The potency and efficacy of such tetra-arginyl or tetra-guanidino compounds can be evaluated using no more than routine experimentation, using assays such as disclosed in Examples 7 et seq.

In the poly-guanidino compounds disclosed herein, when the arginine residues were coupled to amine groups of the center reagents (such as tris(2-aminoethyl)amine, which has three -C-C-N branches extending outwardly from a single center nitrogen atom), the attachment was made through the carboxyl group of the arginine reagent. This causes the fourth nitrogen atom in the arginine molecule (i.e., the alpha nitrogen atom that is normally incorporated into a peptide chain, in proteins) to be converted into a pendant group, rather than inserted into a chain. This pendant amino group is located in the "neck" region of the arginine group, close to the juncture where the arginine is attached to the scaffolding molecule (as shown by the three Boc-protected amine groups in compound [3] in FIG. 1). This arrangement is presumed to further increase the alkalinity and polyamine traits of the resulting molecule. As noted above, these pendant primary amine groups can be regarded as having an intermediate status, midway between the "accessible" amines and the "structural" amines.

Alternatively, a tris-carboxy compound (such as $(HOOC—(CH_2)_x)_3N$, where x is a small integer, such as 1 through 4) can be used as a starting reagent, and the arginine residues can be coupled to the carboxy groups of the tris-carboxy compound through the alpha amine nitrogens of the arginine residues. This would create peptide bonds in the normal manner, with no adjacent pendant primary amine group. Such compounds can be synthesized, and evaluated for neuroprotective efficacy, using routine experimentation as disclosed herein.

It should also be noted that, in di-arginyl compounds such as compound CYP-PA2 (compound [26] in FIG. 2), the two arginine residues are not coupled to each other in an end-toend configuration. Instead, one of the arginine residues is attached to the "alpha" nitrogen atom of the other arginine residue. This generates a branched structure, where the two guanidino groups can act separately from each other, each one attached to the main backbone or scaffolding through its own spacer chain. This further increases the alkalinity and polyamine traits of the resulting molecule, and it provides a total of six highly accessible guanidino groups on each molecule (two branched groups, on each of the three branches). In compound CYP-PA2, these six guanidino groups (each having three nitrogen atoms), are in addition to three primary amine groups, which are pendant and moderately accessible, and the center tertiary amine. As described in the examples, compound CYP-PA2 was shown to provide potent neuroprotective benefits in the in vitro assays, but concerns were raised about its toxicity levels in the $LD_{50}$ assays.

It is also possible to incorporate the "D" isomers of arginine into the compounds disclosed herein. In nature, only "L" isomers of the primary amino acids are normally incorporated into proteins. Accordingly, various reports have indicated that drugs which incorporate D isomers of amino acids, rather than L isomers, are often not degraded as rapidly and have longer effective half-lives, after ingestion or injection, compared to the same compounds which incorporate L isomers.

During an early stage of the research which led to this invention, the Applicant company synthesized and evaluated various polypeptide compounds, using both L-arginine and D-arginine reagents. The in vitro potencies of some of those polypeptide compounds, as measured by ligand blocking assays, are reported in Example 11. As shown therein, various D-arginine compounds had comparable (and in some cases better) blocking potency at N and/or P/Q calcium channels. However, it was recognized by the Applicant that polypeptides probably would not be as effective as non-polypeptide compounds in protecting against neurotoxicity, due to the relatively rapid degradation of polypeptides in the blood. Accordingly, polypeptide compounds (i.e., compounds that are made simply by coupling amino acids together) are not covered by the claims herein.

All of the arginyl-residue non-polypeptide compounds disclosed herein have used L-arginine compounds as reagents. However, it is recognized and believed that D-arginine reagents may be useful for increasing the half-life and neuroprotective efficacy of any of the polyamine compounds disclosed herein, so long as toxicity is not a problem with any such compound (toxicity can be evaluated using various known assays). Accordingly, it is recognized and anticipated that any neuroprotective drugs disclosed herein which include arginine residues or derivatives can be synthesized and tested (for both efficacy and toxicity) using D-arginine reagents, to determine whether the resulting D-isomer compound will have better efficacy than corresponding L-isomer compounds. For various reasons, use of L-isomers is less expensive and more convenient during initial screening tests; however, synthesis and screening of corresponding D-isomers is anticipated for those compounds which show sufficient utility, in in vitro and animal testing, to merit full-scale evaluation in human clinical trials.

It is also recognized by the Applicant that attaching various organic groups (such as methyl, ethyl, and other lower alkyl groups) to various poly-guanidino compounds as disclosed herein may help increase the lipophilicity of those molecules. This may be useful in creating analogs that can more readily cross the blood-brain barrier.

Another method of reducing lipophilicity involves the possible replacement of the double-bonded oxygen, in amide bonds, with hydrogen. This will convert CO groups into $CH_2$ groups. This type of reducing reaction would likely be difficult if attempted on pre-existing amide groups; however, such reduced compounds can be created, if desired, using slightly different reagents and pathways, as known to those skilled in synthetic chemistry.

Assays to Evaluate Potency

A variety of in vitro as well as in vivo tests have been carried out to evaluate pre-synaptic calcium channel blocking potency, and neuroprotective efficacy in living, intact animals. These tests, described in detail in the Examples, include the following:

(1) In vitro tests involving membrane fragments from neuronal cells, as described in Example 7. These tests used competitive binding assays, to determine the potency of the poly-guanidino compounds described herein, in blocking the binding of several selective ligands to various types of calcium channels. This assay does not evaluate actual calcium flow through any channels, and it does not evaluate cellular responses (since the cells have been broken apart and are no longer viable). Instead, this assay is based on the presumption that if a certain poly-guanidino molecule can react with and occupy a certain class of calcium channels, in a manner which prevents a selective ligand from binding to that class of calcium channels even though that ligand has a high affinity for that type of channel, then that polyguanidino compound is likely to also be capable of reducing calcium ion flow through that class of channel. This presumption has been borne out; the specific polyamines that showed the most potent blocking activity against ligands, in the membrane fragment tests, became primary candidates in subsequent hippocampal tissue tests. During the hippocampal tissue tests (and later, during the in vivo tests), a strong positive correlation was seen between combined N and P/Q channel blocking potency, in the ligand blocking assays, and neuroprotective potency in the subsequent assays.

(2) Additional in vitro tests involving perfused slices of hippocampal tissue from the brains of sacrificed rats, as described in Example 8. Various poly-guanidino candidates with good combinations of N-channel and P/Q-channel blocking potency (as shown in the ligand blocking assays of Example 7) were tested to determine their ability to protect hippocampal neurons against damage during and after a period of tissue hypoxia. The selected poly-guanidino compounds all showed neuroprotective effects, as evidenced by the ability of neurons in poly-guanidino-treated tissue segments to recover, and to continue firing (transmitting nerve impulses) in a much more normal manner, compared to untreated tissue segments, after oxygen was resupplied to the treated or untreated tissue segments.

At roughly the same time as the hippocampal tissue tests were being carried out, various polyamine compounds were also tested in toxicity tests, using conventional $LD_{50}$ tests in mice. These tests showed that compound CYP-PA2 (the di-arginine compound shown in FIG. 2) had an $LD_{50}$ level of about 125 mg/kg. By comparison, the CYP-PA1 compound appeared to be completely free of any toxicity concerns, even at the highest dosages tested (200 mg/kg). According, subsequent in vivo tests focused mainly on the CYP-PA1 compound.

(3) In vivo tests using surgically-induced ischemia in adult mammalian lab animals (gerbils), as described in Example 10. The CYP-PA1 and CYP-PA2 poly-guanidino compounds were both tested, and both were shown to provide substantial and beneficial protection against actual ischemia, in a mammalian species that is widely used in ischemia research.

It is important to note that, in these in vivo tests, the poly-guanidino compounds were found to be effective in protecting against brain damage, even though the drugs were injected into the peritoneal (abdominal) cavities of the test animals. This confirms the ability of these poly-guanidino compounds to penetrate mammalian blood-brain barriers (BBB's). This trait is essential in providing convenient and useful routes of administration, such as simple intravenous injection, that do not require injection of the protective drug through a hole drilled into the skull, directly into a brain ventricle.

Various other screening tests to assess neuroprotective efficacy are also known to those skilled in the art. By way of example, lab animals such as rats can be treated with convulsant drugs or electroshock treatments which, in unprotected animals will induce convulsions or other easily observable behavioral changes. If a poly-guanidino compound can reduce the severity or occurrence rate of such convulsions or other behavioral abnormalities in such animals, such suppression indicates that the compound being tested has neuroprotective properties. If its neuroprotective properties are significantly better than other benchmark compounds, such as diazepam (widely used under the trademark VALIUM, an anxiolytic drug that is widely used in research as an anti-convulsant drug), then it may merit closer evaluation in more complex and expensive tests.

This pre-synaptic calcium channel blocking activity allows certain poly-guanidino compounds, as disclosed herein, to suppress and control excessive neuronal activation, which in turn controls and reduces the release of potentially excitotoxic neurotransmitters. By showing a direct correlation between pre-synaptic calcium channel blocking potency and neuroprotective efficacy, this invention discloses a clear and direct correlation between an easily measured in vitro activity, which can be determined for any candidate compound using routine screening tests, and an extraordinarily valuable therapeutic benefit for patients suffering or at risk of excitotoxic brain damage.

In addition to helping protect CNS neurons against excitotoxic damage due to conditions such as stroke, cardiac arrest, and other forms of ischemia or hypoxia, the poly-guanidino compounds of this invention are also believed to be useful to help control and reduce certain other types of unwanted excessive neuronal activity, including neuropathic pain (i.e., the type of chronic pain that does not respond well to treatment by opiate analgesics). Certain other classes of polyamine compounds that can suppress calcium ion flow through neuronal calcium channels have previously been shown to be useful in treating certain types of pain, including neuropathic pain; accordingly, it is believed that at least some of the compounds in the class disclosed herein are highly likely to exert the same types of pain-reducing effects, when used on patients who suffer from such forms of pain.

Modes of Administration and Packaging

For acute indications such as stroke, cardiac arrest, or head trauma, poly-guanidino compounds which control pre-synaptic calcium activity may be administered by injection, either via single-injection bolus or via continuous infusion. Typical dosages are likely to be in the range of about 2 to about 20 mg/kg intravenously (IV) immediately or as soon as possible after the establishment of reperfusion (within 3 hours). Doses administered by bolus injection can be repeated at 3–12 hour intervals for several days after the acute event. Alternately, administration may be by direct infusion into the brain. For example, if a patient is undergoing brain surgery to repair a burst aneurysm or remove a brain tumor, a cannula can be placed in the brain which will deliver a neuroprotective poly-guanidino compound directly to the affected region or into a cerebral ventricle. If desired, the cannula can be attached to an osmotic mini-pump, or to an implanted slow-release device which can use (for example) a polymer sold under the trademark ELVAX (DuPont Company, Wilmington, Del.), which releases the compound slowly over a sustained period.

Poly-guanidino drugs as described herein can also be used for neuroprotection purposes in patients undergoing surgery, such as cardiac surgery where the patient must be placed on cardiopulmonary bypass (a so-called heart-lung machine), or when patients are undergoing endarterectomy to remove plaques from the insides of arterial walls. The drug can be administered in sterile saline via the intravenous route starting 30 minutes before the surgery. The infusion rate is at a rate of between 0.1 to 1.0 mg/kg/minute and is continued for the duration of the procedure. The drug decreases the degree and extent of neurological damage resulting from the ischemia induced by the surgical procedure. Neurologic status after surgery can be assessed by standard cognitive function tests.

Administration to experimental animals can be either intravenous or intraperitoneal at doses ranging from 0.25 to 100 mg/kg. The preferred dose is between 0.5 and 5 mg/kg. The dosing is done before the induction of ischemia or up to 1 hour afterwards and repeated at 3 hours and 12 hours post-reperfusion.

For most poly-guanidino compounds, oral administration is likely to be relatively inefficient, largely due to the slow absorption of highly ionized molecules through the intestinal walls. Accordingly, for longer-term treatment of problems such as epileptic, trauma-induced, or other seizures, or for treating neurodegenerative diseases which involves excitotoxic overstimulation of neurons as a component of the disease, implantation of a slow-release device (such as an osmotic mini-pump) may be preferable if a poly-guanidino compound is used which is not readily absorbed into the blood through the intestinal walls. Alternately, oral administration of certain types of poly-guanidino compounds may be feasible if appropriate enhancement techniques are used, such as using enteric coatings to prevent hydrolysis in the stomach, and coupling the desired chemical structure to a carrier molecule or pro-drug form that increases absorption into the blood after oral ingestion.

The neuroprotective poly-guanidino compounds disclosed herein can be formulated and packaged in various ways that render them practical and convenient for use in various medical settings. For example, they can be prepared as injectable liquid formulations, if mixed with a liquid carrier substance (such as an isotonic saline solution) that renders the formulation suitable for intravenous injection into humans. Alternately, they can be dehydrated by suitable means such as lyophilization (i.e., freezing an aqueous preparation and then subjecting it to a vacuum to remove water molecules), to provide a dried or semi-dried formulation such as a powder or cake, which can be reconstituted for use by mixing it with a liquid carrier substance.

A convenient mode of packaging for a sterile and stable dehydrated poly-guanidino compound as disclosed herein comprises a glass vial (such as a lyophilization vial, as known in the art) sealed with a watertight stopper that can maintain the sterility of the drug contained therein. Accordingly, this invention discloses an article of manufacture, comprising (i) a sealed watertight container capable of maintaining sterility of the chemical contents therein, and (ii) a sterile drug preparation comprising a neuroprotective poly-guanidino compound as disclosed herein.

Salts, Analogs, and Derivatives

In addition to specific poly-guanidino compounds discussed herein, salts or isomers (including stereoisomers) of such poly-guanidino compounds can be used, provided that they are pharmaceutically acceptable, and therapeutically effective when used as described herein. The term "pharmaceutically acceptable" embraces those characteristics which make a drug suitable and practical for administration to humans. Although this is not a comprehensive list, the most directly relevant criteria include: (1) suitable compounds must be sufficiently chemically stable under reasonable storage conditions to have an adequate shelf life; (2) they must be physiologically acceptable (non-toxic, non-carcinogenic, etc.); (3) they must be capable of penetrating the blood-brain barrier, if introduced into circulating blood; and, (4) they must have a sufficiently long half-life in circulating blood (which requires resistance to rapid enzymatic degradation) to be therapeutically effective when administered in reasonable and practical dosages. In addition, the term "neuroprotective" indicates that a poly-guanidino compound with a molecular structure covered by the claims must indeed be effective, as a neuroprotective agent, in human patients, in order to be covered by the claims. This requirement of efficacy requires any such compound to be "pharmaceutically acceptable", in order to be covered by the claims herein.

Acceptable salts can include alkali metal salts as well as addition salts of free acids or free bases. Examples of acids which may be employed to form pharmaceutically acceptable acid addition salts include inorganic acids such as hydrochloric acid, sulfuric acid and phosphoric acid, and organic acids such as maleic acid, succinic acid and citric acid. Alkali metal salts or alkaline earth metal salts might include, for example, sodium, potassium, or magnesium salts. All of these salts may be prepared by conventional means. The nature of the salt is not critical, provided that it is non-toxic and does not substantially interfere with the desired activity.

The terms "analogs" and "derivatives," which refer to variants of the specific compounds disclosed herein, are used herein in a conventional chemical sense. An analog is a molecule which resembles another designated molecule, but which has been modified by one or more substituted or altered chemical groups. For example, in an analog, a specific hydrogen atom or hydroxyl group attached to a molecule at a certain location might be replaced by halogen atoms, alkyl or acyl groups, or various other chemical substituents. If the resulting analog still has the full set of desirable properties discussed herein, it may be useful for neuronal protection against ischemic or hypoxic damage, as disclosed herein. Certain analogs may have somewhat greater potency than a referent molecule, and may therefore rise to the level of an improvement; nevertheless, if it is created and tested for neuroprotective efficacy based on the teachings herein, it remains within the reach of any claims which refer to such analogs.

One class of analogs that are of interest herein include analogs that have been modified in ways designed to render them more capable of permeating through the blood-brain barrier (BBB). The electrochemical traits of molecules that either can or cannot permeate through mammalian BBB's are reasonably well understood, and strategies have been developed for modifying drug molecules in specific limited ways that are designed to increase their ability to permeate through BBB's. Any such known and conventional technique can be evaluated for use as described herein, to increase the neuroprotective potency and efficacy of the poly-guanidino compounds disclosed herein.

It also should be noted that "analogs" is not used or intended herein to cover conjugates (i.e., molecules in which two different molecules, having two different functions, are bonded to each other to form a new molecule having new characteristics). Typically, conjugates are used for purposes such as (1) providing two different functions in a single molecule; (2) creating pro-drugs that will be protected against chemical or enzymatic degradation until they reach the useful therapeutic site; and (3) providing a "carrier" system that will help transport a "payload" drug to a site where it is needed. In general, conjugates make qualitative (rather than merely quantitative) changes in their component molecules; they provide significantly new traits, rather than merely varying the degree of a trait such as potency, toxicity, etc. By contrast, "analogs" normally differ only in degree, such as by being somewhat more or less potent than a referent molecule in a known and previously-identified activity.

As used herein, "derivative" refers to a molecule which is derived from a designated starting (referent) molecule. Unlike analogs, which can be created via separate pathways, a derivative must be created by chemical treatment of the referent molecule.

This invention anticipates that various analogs and derivatives of the specific poly-guanidino compounds listed herein will be synthesized, using standard chemical synthesis procedures, and that they will be tested for neuroprotective activity, using the assays described in the tests discussed herein, and by other assays which evaluate neuroprotective activity, known to those skilled in the art. If such compounds prove to be more effective than the specific poly-guanidino compounds listed herein in controlling pre-synaptic calcium channel activity and in preventing excitotoxicity, such analogs or derivatives may rise to the level of patentable improvements. Nevertheless, if they follow from the disclosures herein and are analogs or derivatives of the specific compounds listed herein, they are within the scope of the subject invention.

EXAMPLES

Throughout the Examples, the following abbreviations apply:

DCC refers to dicyclohexylcarbodiimid (purchased from Aldrich Chemical Company, Milwaukee, Wis., catalog #D8,000-20);

HOBt refers to N-hydroxybenzotriazol (Aldrich catalog #BP600-100);

DIEA refers to N,N-diisopropylethylamine (Aldrich catalog #BP592-500)

TFA refers to trifluoroacetic acid;

DMF refers to dimethyl formamide;

Boc-Arg(Pmc)-OH refers to N-α-tertiary-butyloxycarbonyl-$N_G$-2,2,5,7,8-pentamethylchroman-6-sulfonyl-L-arginine (Bachem Chemical Company, King of Prussia, Pa., catalog number A2875);

Boc-Arg(Mtr)-OH refers to N-α-tertiary-butyloxycarbony-$N_G$-(4-methoxy-2,3,6 trimethylbenzene sulfonyl)-L-arginine (Novabiochem, San Diego, Calif, catalog #04-12-0113);

Boc refers to a butyloxycarbonyl protective group, in a larger molecule;

Cbz refers to a carbobenzyloxycarbonyl protective group, in a larger molecule;

Pmc refers to a pentamethylchroman-6-sulfonyl protective group, in a larger molecule;

Mtr refers to a 4-methoxy-2,3,6-trimethylbenzene sulfonyl protective group, in a larger molecule;

H-Arg(Pmc)-OH refers to $N_G$-2,2,5,7,8-pentamethylchroman-6-sulfonyl-L-arginine (Novabiochem, San Diego, Calif., catalog # 04-12-5258);

(Cbz)Arg(Cbz)$_2$-OSu refers to N-α,$N_G$,$N_G$-tri-Cbz-L-arginine-N-hydroxysuccinimide ester (Novabiochem, San Diego, Calif., catalog # 04-12-0538).

All reactions were carried out at room temperatures, unless otherwise indicated.

Example 1

Synthesis of tris(arginyl-2-aminoethyl)amine

The synthetic pathway used to create tris(arginyl-2-aminoethyl)amine is shown in FIG. 1. In this synthesis, Boc-Arg(Pmc)-OH (4.13 g; 7.6 mmole; shown as compound [11] in FIG. 1) was dissolved in 50 mL of dry $CH_2Cl_2$. An activated ester, modified at the #1 carbon atom in the arginine structure, was generated by carboxyl activation, using HOBt (1.18 g, 7.6 mmole) in the presence of equimolar DCC (1.58 g, 7.6 mmole), which scavenged the water molecules released by the ester-forming reaction. This ester (which was not isolated or purified, but was consumed in situ) was then coupled with tris(2-aminoethyl)amine (96%, Aldrich Chemical Co., catalog #22-563), which is shown as compound [12]) (0.178 mL, 1.26 mmole). A precipitate of dicyclohexyl urea formed, from the reaction between DCC and water. The reaction mixture was stirred at room temperature for 6 hours to yield a protected intermediate, shown as compound [13], in which both Pmc and Boc protective groups were present on each of the three arms. Thin layer chromatography (TLC), using a tiny amount of the product placed on silica gel with 10% MeOH in 90% $CHCl_3$ as the solvent, showed that this protected intermediate (compound [13]) had an $R_f$ value of 0.6 (which indicates the distance that was travelled by the compound, divided by distance travelled by the solvent front).

The precipitate of dicyclohexyl urea was filtered off and discarded, and the solvent ($CH_2Cl_2$) was removed under reduced pressure (about 30 torr). The residue was redissolved in ethyl acetate and washed with water (3 times, using 50 mL each; all water used herein was deionized). The combined organic layer was dried (i.e., residual water was removed) with anhydrous $MgSO_4$. After filtration using a glass frit, to remove the $MgSO_4$ and bound water from the solution, the solvent was removed on a rotary evaporator. The intermediate [13], still protected by the Boc and Pmc groups, was dried using a high vacuum (about 0.05 torr). A yield of 6.8 g of crude intermediate was obtained.

This protected intermediate [13] was purified by silica gel column chromatography (silica gel 60 Å, 70–230 Mesh ASTM, Whatman Company, Clifton, N.Y., # 4791 010). The column was eluted with a stepwise gradient, initially using 100% $CHCl_3$, followed by 10% MeOH in $CHCl_3$, then by 20% MeOH in $CHCl_3$. Elution fractions which contained the desired protected intermediate [13] (as indicated by TLC confirmation) were combined, evaporated, and dried in high vacuum to give 3.1 g of purified intermediate [13].

To remove the PMC and BOC protective groups, purified intermediate [13] was treated with 50 mL TFA in the presence of 2.5 mL thioanisole, 1.25 mL water, and 1.25 mL ethanedithiol. After 4 hours stirring at room temperature, cold ether (200 mL) was added, to cause precipitation of the final de-protected product, shown as compound [14] in FIG. 1. The white precipitate was collected and washed with ether. The precipitate was lyophilized at high vacuum, and yielded 2.85 g of crude product.

Purification was performed by preparative high performance liquid chromatography (HPLC; Waters Prep LC 4000 system) using a reverse-phase column (Millipore, Bedford, Mass., Delta-Pak C18, 40×100, 15 μm, 100 Å). Peaks were observed using Waters 486 Tunable Absorbance Detector (at 214 nanometers wavelength). Solvents used for HPLC elution were (A) water containing 0.1% TFA, and (B) 60% acetonitrile in water containing 0.1% TFA. The column was eluted with a linear gradient, beginning with 100% A which changed to 70% A and 30% B over 30 minutes, at a flow rate of 50 ml/min. Based on UV absorption peaks, the fraction that emerged while the column was being eluted with 14% B was collected and lyophilized. To confirm purity, analytical HPLC was performed using a Waters Symmetry column (C18, 3.9×150 mm, 5 μm, 100 Å) and a Gilson HPLC System (25 WTI pump heads). Peaks were observed using a Gilson 117 UV Detector (214 nanometers). The column was eluted using the same gradient as above over the course of 53 min and at a flow rate of 1 mL/min. This indicated that the fraction contained the desired compound [14] with no detectable impurities.

523 mg of compound [14], in form of the TFA salt, were obtained. This compound was a white powder, with a molecular formula of $C_{24}H_{54}N_{16}O_3$ (as the free amine compound, without the TFA salt), with a calculated molecular weight of 614.80. Mass spectrum analysis using electrospray, performed at an independent lab (Mass Consortium, San Diego, Calif.), indicated an ion with a mass of 616 daltons and a single positive charge (corresponding to M+H$^+$).

Compound [14], shown as the final product in FIG. 1, was given the company designation CYP-PA1, where "CYP" refers to Cypros Pharmaceutical Corporation and "PA" refers to polyamine. The chemical name is tris(arginyl-2-aminoethyl)amine.

It should be noted that the reactions described above caused the arginine residues (supplied by reagent [11]) to be coupled to the tri-amine compound (reagent [12]) in a manner which coupled the carboxy group of the arginine residue to the primary amine groups at the ends of the three arms of the triamine reagent. This created an amide bond in each of the three arms, and allowed the primary amines in the arginine residues to remain accessible.

Example 2

Synthesis of Tris(arginyl-arginyl-2-aminoethyl) amine (Cbz)Arg(Cbz)$_2$-OSu (5 g, 7.42 mmole; shown as compound [21] in FIG. 2) was dissolved in 20 mL of dry $CH_2Cl_2$. DIEA was added, in a 2:1 molar ratio (2.73 mL, 14.84 mmole). H-Arg(Pmc)-OH (3.26 g, 7.42 mmol; shown as compound [22]) was dissolved in 10 mL of dry DMF, then added to the (Cbz)Arg(Cbz)$_2$-OSu solution. The mixture was stirred at room temperature for 2 hours. This caused the only primary amine on compound [22] which was not protected to displace the succinimide ring structure of compound [21].

This created a protected di-arginyl intermediate, with three Cbz and one Pmc protecting groups attached to it, shown as compound [23] in FIG. 2. TLC was performed, using a small quantity of the solution, on precoated silica gel plates (Whatman, Clifton, N.Y., # 4420 222), which were developed using MeOH/CHCl$_3$ (20:80). The TLC plates were visualized with UV light and/or 2% ninhydrin in EtOH. The desired product had an Rf value of 0.7.

After TLC confirmation that the reaction had proceeded to completion, the solvent was removed by rotary evaporation, and the residue (which contained compound [23]) was redissolved in ethyl acetate and washed with water (3 washings, 50 mL each). Residual water was removed from the organic layer, using anhydrous MgSO$_4$. After filtration to remove the MgSO$_4$, removal of most of the solvent under low vacuum, and complete drying under high vacuum, 7.1 g of crude intermediate [23] was obtained. Analytical HPLC and mass spectra analysis were performed for this intermediate.

Five grams (5 mmol) of this compound [23] were dissolved in 50 mL of dry $CH_2Cl_2$. Compound [23] was then converted into an active ester, by carboxyl activation, using HOBt (675 mg, 5 mmole) in the presence of DCC (1.030 g, 5 mmole), which scavenged the water molecules released by the ester formation, as described above in Example 1.

The resulting activated ester was then reacted with a three-armed tri-amine compound, tris(2-aminoethyl) amine (96%, Aldrich, catalog # 22-563, 0.123 mL, 0.83 mmole; shown as compound [24] in FIG. 2 (this is the same tri-amine compound 30 used in Example 1). This caused the di-arginine group (compound [23]) to be coupled to each of the three arms of the tri-amine (compound [24]), through the only unprotected carboxy group on compound [23]. The reaction was stirred at room temperature for 4 hours, and dicyclohexyl urea precipitated during the coupling. TLC in 10% MeOH in CHCl$_3$ showed that the desired intermediate compound [25], had an R$_f$ value of 0.6. In this intermediate, one Pmc and three Cbz protective groups remained attached to each of the di-arginyl arms.

The precipitate was filtered off, and solvent was removed under mild vacuum. The residue was redissolved in ethyl acetate and washed with water (3×50 mL). After filtration, water was removed from the organic layer using anhydrous MgSO$_4$. The solvent was evaporated and the product was dried under high vacuum to yield 7 g of compound [25].

Purification was performed by silica gel column chromatography (silica gel 60 Å, 70–230 mesh ASTM, Whatman, Clifton, N.Y., catalog # 4791 010). The column was eluted with a stepwise gradient which began at 3% MeOH in CHCl$_3$ and increased to 10% MeOH in CHCl$_3$. Fractions which contained the desired product (as indicated by TLC) were collected and pooled, concentrated on a rotary evaporator, and dried. A yield of 1.022 g was obtained. Purity was confirmed by analytical HPLC, and the intermediate [25] was dried under vacuum.

To remove the protective groups, compound [25] (1.022 g; 0.25 mmole) was dissolved in 50 ml of 50% $CH_2Cl_2$ and 50% MeOH. Palladium on activated carbon (Aldrich Company, catalog # 20,569-9; 10% charcoal, 300 mg) and 3 mL of formic acid (Fluka Company, Ronkonkoma, N.Y., catalog # 06450) were added, at room temperature. Hydrogen was bubbled through this solution for 5 hours. After filtration, the solvent was removed with a rotary evaporator. This created another intermediate, with no Cbz protective groups but with the Pmc groups still attached.

This intermediate was then treated with TFA (30 mL), in the presence of thioanisole (1.2 mL), water (1 mL), and ethanedithiol (0.8 mL) for 10 hours, to remove the Pmc protective groups. Cold ether (200 mL) was then added, to complete the precipitation of the crude product. The white precipitate was collected and washed with ether. The crude product was lyophilized under high vacuum, and yielded 540 mg of the final product, shown in two different ways as compound [26] in FIG. 2.

Purification was performed using Waters (Millipore, Bedford, Mass.) column (Delta-Pak C18, 40×100, 15 mm, 100 Å) and Waters Prep LC 4000 system. Peaks were observed using Waters 486 Tunable Absorbance Detector (214 nanometers). Solvents used for HPLC elution were (A) H$_2$O containing 0.1% TFA, and (B) 60% acetonitrile in H$_2$O containing 0.1% TFA. The column was eluted with a linear gradient of 0% solvent B to 30% B in solvent A, over the course of 30 minutes, at a flow rate of 50 ml/min.

The fraction which emerged from the column at 18% B was collected and lyophilized. 260 mg of the desired compound [26], in form of the TFA salt, were obtained. This compound was a white powder, with a molecular formula of $C_{42}H_{90}N_{28}O_6$ (as the free amine compound, without the TFA salt), with a calculated molecular weight of 1083.36.

Mass spectrum analysis indicated a mass of 1084 daltons, and a single positive charge (M+H$^+$)

Compound [26] was designated as CYP-PA2.

Example 2A

Semi-Saturated Di-Arginyl Compound

During the purification of Compound [26], shown in FIG. 2, it was observed that a by-product was obtained which performed (during chromatography) in a manner which suggested that it had di-arginyl groups attached to only two of the three arms of compound [24]. This "semi-saturated" compound was purified using preparative HPLC, and evaluated by mass spectrum analysis, which indicated a mass of 771 daltons, and a single positive charge (M+H$^+$).

This semi-saturated compound, designated as CYP-PA2X, was tested in the neuronal fragment assays (to evaluate calcium channel blocking potency) described in Example 9, and in the hippocampal tissue assay (to evaluate neuroprotective potency in vitro), described in Example 10. In both assays, it was not as potent as the fully di-arginylated compound CYP-PA2 (compound [26]), which has six arginine residues, two on each arm.

Example 3

Synthesis of mesityl-tris-arginine

Boc-Arg(Mtr)-OH (0.89 g, 1.8 mmole), shown as compound [31] in FIG. 4, was dissolved in dry DMF (20 ml) and pyridine (2 ml). HOBt (0.3 g, 2 mmole) was added, and DCC (0.4 g, 1.9 mmole) that had been dissolved in dry DMF (5 ml) was also added. The mixture was stirred for an hour at room temperature. As in Examples 1 and 2, this generated an active ester group on the protected arginine.

This ester compound was mixed with 1,3,5-tris-(aminomethyl)-benzene (shown as compound [32] in FIG. 3), which had been synthesized as described in JACS 101: 2728–2731 (1978), in benzene (2 ml). The mixture was stirred for 14 hours at room temperature. Dicyclohexyl urea precipitated, and was removed by filtration. The product was precipitated by the addition of water, collected, and concentrated with a rotary evaporator. TLC in 15% MeOH in CHCl$_3$ showed that the desired product had an R$_f$ value of 0.5. After drying, 0.43 g of a protected intermediate, 1,3,5-tris(Boc-Arg(Mtr)-amidomethyl)-benzene, shown as compound [33] in FIG. 4, was obtained.

To remove the Boc and Mtr protective groups and create a tris-arginyl compound with a single arginine residue on each of the three arms attached to the center benzene ring, one aliquot of protected intermediate [33] was treated with TFA (in the presence of thioanisole, water, and ethanedithiol) for 20 hours, as described in the final deprotection step of Examples 1 and 2. This generated the final compound [34], which was designated as CYP-PA3.

The other aliquot of intermediate [33] was converted into a hexa-arginyl compound, as described in Example 4.

Example 4

Synthesis of mesityl-hexa-arginine

To create a hexa-arginyl compound having a di-arginyl structure on each of three arms, the protected intermediate [33] (0.285 g, 0.18 mmole) described in Example 3 was dissolved in TFA (2 ml) for 20 minutes, with stirring, to remove the Boc protective groups but not the Mtr protective groups. This generated intermediate [41], with an unprotected primary amine coupled to the "neck" region of each of the three arginine groups.

This intermediate [34] was then mixed with an additional quantity of Boc-Arg(Mtr)-OH reagent (shown as compound [31] in FIG. 3) which had been converted into an active ester by HOBt and DCC, as described above. This mixture was stirred at room temperature for 14 hours. The carboxylic acid group in the Boc-Arg(Mtr)-OH reagent reacted with the de-protected primary amine in the "neck" region of each of the three arginine groups, to create a protected di-arginyl structure on each of the three branches. Dicyclohexyl urea precipitated, and was removed by filtration. The intermediate was precipitated by the addition of ether, collected, and concentrated with a rotary evaporator. A colorless, viscous oil was obtained using silica gel chromatography with 5% MeOH in CHCl$_3$.

To remove the Boc and Mtr protective groups, the hexaarginyl compound was treated with TFA (5 ml) in the presence of thioanisole, water, and ethanedithiol, as described above, for an additional 14 hours. The crude product was precipitated by the addition of diethyl ether. This generated 1,3,5-tris(argininyl-arginyl-amidomethyl)-benzene as a TFA salt (26 mg, 14% yield). This is the final compound [42], shown in two different ways at the bottom of FIG. 4. Purification was performed by HPLC. NMR and mass spectra analysis confirmed its molecular structure. This compound was designated as CYP-PA4.

It should be noted that Examples 2 and 4 describe two different methods for creating branched polyamine groups. In Example 2, a di-arginyl compound was created, then three copies of that di-arginyl molecule were attached to a center molecule. This created a final compound having six accessible guanidino groups, at the ends of six distinct branches. By contrast, in this Example 4, a tris-arginyl compound was created, with three single arginine residues coupled to a center benzene ring. Subsequently, three more arginine residues were attached to that molecule, one on each arm, using primary amine groups on each arm, in a method which increased the number of accessible amine groups without blocking or hindering the three guanidino groups that had previously been attached to the scaffolding molecule. As in Example 2, this approach resulted in a total of six accessible guanidino groups, at the ends of six distinct branches, along with three additional primary amine groups, in the "neck" region of each sub-branch formed by the addition of the second arginine residue.

Example 5

Synthesis of Tetra-arginyl Compound with Center Carbon Atom

As an alternative to the various three-branched compounds disclosed above, it is also possible to synthesize similar compounds having four branches, extending outwardly in a radial manner from a center carbon atom.

One such synthetic method, illustrated in FIG. 5, begins with a compound called "pentaerythritol", which has four methyl-hydroxy groups attached to a center carbon atom in a radial configuration. This compound, shown as compound [51] in FIG. 5, can also be called tetra-methylol-methane, or 2,2-bis(hydroxymethyl)-1,3-propanediol, or tetrakis (hydroxymethyl)methane. It is commercially available from suppliers such as Aldrich Chemical Company.

The four hydroxy groups can be converted into four primary amine groups, by means of a two-step method. In the first step, the pentaerythritol is treated with chlorotrimethylsilane and sodium cyanide, in the presence of a catalytic amount of sodium iodide, according to a procedure described in *J. Org. Chem.* 46: 2985 (1981). This treatment step will substitute the hydroxy groups with cyano groups, —CN, to create a nitrilo group (—CH$_2$CN) at each of the termini of the four short branches. The resulting intermediate, shown as compound [52] in FIG. 5, can be called 1,3-dinitrilo- 2,2-bis-(methylenenitrilo)-propane. It can be purified by a washing procedure followed by silica gel chromatography.

In the second step, the tetra-nitrilo intermediate [52] can be reduced with sodium borohydride (NaBH$_4$) in the presence of cobalt(II) chloride hexahydrate (COCl$_2$.6H$_2$O), using a procedure described in *J. Amer. Chem. Soc.* 67: 108 (1986). After the reaction is completed, water can be added to hydrolyze any excess sodium borohydride. The aqueous phase can be acidified and washed with methylene chloride, and sodium hydroxide can be added to the aqueous phase until it becomes alkaline. The resulting intermediate can be extracted several times with ethyl acetate. The combined organic phases can be dried with sodium sulfate, filtered, and evaporated, to give the tetra-amine intermediate having a primary amine group at the end of each of the four short chains, which can be called 1,3-diamino-2,2-bis(methyleneamino)-propane, shown as compound [53] in FIG. 5.

This tetra-amino intermediate [53] can then be converted into a tetra-arginyl compound, by reacting it with a protected arginine reagent, such as the Boc/Pmc arginyl reagent shown as compound [11] in FIG. 1. This coupling reaction is shown on the left side of FIG. 5, and it generates a Boc/Pmc-protected tetra-arginyl intermediate [54]. The Boc and Pmc groups are then removed by hydrolysis using TFA, to provide the final compound [55], which can be called by various chemical names, including tetrakis(arginyl-2-aminoethyl)methane.

Alternately, as shown on the right side of FIG. 5, the tetra-amino intermediate can be converted into a tetra-guanidino compound, by using a guanylating agent (discussed below, in Example 6) to add an amidine group (with two nitrogens) to each of the four primary amine groups, thereby converting each primary amine group into a guanidino group having three nitrogen atoms. This final product can be called tetrakis(guanidinomethyl)methane, and is shown as compound [60] in FIG. 5.

It is believed that these tetra-arginyl or tetra-guanidino compounds are likely to have comparable blocking and suppressing activity at N-type and P/Q-type calcium channels, and that they are likely to be useful as neuroprotective agents. The potency of any such compound, when used for such neuroprotective purposes, can be evaluated using in vitro channel-blocking assays such as disclosed in Example 7, in vitro hippocampal slice protection assays such as described in Example 8, and suitable in vivo models of cerebral ischemia such as the models disclosed in Example 10.

Example 6

Conversion of Primary Amines into Guanidino Groups

If desired, a primary amine group (i.e., R-NH$_2$) can be converted into a guanidino group, by means of a relatively simple reaction, to increase the number of accessible amine groups on a compound that is being evaluated or optimized for neuroprotective activity. This reaction can use any of several known "guanylating" agents, such as 1H-pyrazole-1-carboxamidine; 2-methyl-2-thiopseudourea; O-methylisourea; formamidinesulfonic acid; 3,5-dimethylpyrazole-1-carboxamidine nitrate; N-[bis(methylthio)-methylene]-p-toluene-sulfonamide; cyanamide; and various forms of these reagents which have protective groups such as Boc, Pmc, or Mtr. These reagents are available commercially, from companies such as Aldrich Chemical Company. Since some of these compounds are highly alkaline, they are sometimes mixed with an acid, such as hydrochloric acid or sulfuric acid, to form a relatively stable salt form, such as the hydrochloride salt or the hydrogen sulfate salt.

When a guanylating reagent is reacted with a compound having a primary amine group, one of the hydrogen atoms of the primary amine group will be displaced by a diamine component (which often is an amidine group, as shown in FIG. 5) from the guanylating reagent. When the two nitrogen atoms having a suitable structural arrangement from the diamine component are added to the original nitrogen atom from the primary amine group, the resulting three-nitrogen group comprises a guanidino group at the location where the primary amine had been located. This method can be used to convert either a "terminal" primary amine (i.e., an —NH$_2$ amine group at the end of a chain), or a "pendant" primary amine (i.e, an —NH$_2$ group bonded to a carbon atom in the middle of a chain) into a guanidino group.

An example of this approach is shown on the right side of FIG. 5, in the synthesis of compound [60], which is not a radial arginine compound but which resembles a radial arginine compound in several important respects. Various other similar compounds can be created with a center nitrogen atom and three branches rather than four, by using reagents such as tris(aminomethyl)amine. Similarly, other comparable products having identical center groups and identical functional amine groups at the end of each branch can be created, by using branched reagents having different spacer chains, such tris(2-aminoethyl)amine, tris(3-aminopropyl)amine, or tris(4-aminobutyl)amine.

Similarly, a tris-guanidino benzene compound can be created, using relatively simple methods and inexpensive reagents, by treating a reagent such as 1,3,5-tris (aminomethyl)-benzene (shown as compound [32] in FIG. 3, discussed in Example 3) with a guanylating agent. The resulting compound can be called 1,3,5-tris (guanidinomethyl)-benzene. Other similar compounds with a center benzene ring and spacer chains having different lengths can be created by using starting reagents such as 1,3,5-tris-(2-aminoethyl)-benzene, 1,3,5-tris-(3-aminopropyl)-benzene, or 1,3,5-tris-(4-aminobutyl)-benzene.

One advantage of this approach which uses direct guanylating agents, rather than arginyl reagents, is that it may allow the use of relatively simpler and less expensive reagents than the protected arginyl reagents that were used to create radial poly-arginyl compounds such as CYP-PA1 through CYP-PA4.

The guanylated compounds disclosed in FIG. 5 and in this Example are believed to be useful as neuroprotective agents, to inhibit calcium ion entry into neurons via N-type and P/Q-type calcium channels. The potency of any such candidate compound, and the levels of toxicity or other adverse side effects, can be evaluated through routine experimentation using the in vitro and in vivo assays disclosed in the following examples, or using other assays known to those skilled in the art.

Example 7

In Vitro Blockage of Channel-Specific Ligands

The polyamine compounds created as described in Examples 1 through 4 were assayed for their ability to inhibit channel-specific binding of certain ligands to N-type, P/Q-type, or L-type calcium channels, using neuronal membranes obtained from rat brains.

The neuronal membranes were isolated and prepared according to standard methods (e.g., Wagner et al 1988). Calcium channels were identified by the binding of $^{125}$I-labelled omega conotoxin fragments, or $^{3}$H-labelled dihydropyridines. Conotoxin GVIA (G6A) was used as an irreversible ligand for neuronal N-type channels; conotoxin MVIIA (M7A) was used as a reversible ligand for neuronal N-type channels; and conotoxin MVIIC (M7C) was used as a ligand for P/Q channels (all of these omega conotoxins were labelled with $^{125}$I). $^{3}$H-labelled PN200-110 or $^{3}$H-nitrendipine was used to label L-type calcium channels.

Prepared membrane fragments were incubated with various concentrations of (1) the poly-guanidino compounds synthesized as described herein, and (2) radiolabelled ligand. The membranes were then washed to remove excess ligand. The membrane fractions were harvested with a Brandel cell harvester over glass fiber filters, and radioactivity was assessed by counting the filters in a gamma counter, or by liquid scintillation spectrophotometry (Wagner et al 1988). The concentrations of the poly-guanidino compounds required to inhibit binding of calcium channel ligands by 50% ($IC_{50}$) were determined. These values are listed in Table 1. In all tables, "N.T." indicates "Not Tested".

TABLE 1

CHANNEL-SPECIFIC LIGAND BLOCKING
BY RADIAL POLY-GUANIDINO COMPOUNDS
IC50 VALUES (MICROMOLAR)

| COMPOUND | GVIA = G6A (N Type) | MVIIA = M7A (N Type) | MVIIC = M7C (P/Q Type) | PN200 (L Type) |
|---|---|---|---|---|
| CYP-PA1 | 3.60 | 2.10 | 0.40 | >300 |
| CYP-PA2 | 0.90 | 0.20 | 0.06 | >100 |
| CYP-PA2X | 2.50 | 0.87 | 0.16 | N.T. |
| CYP-PA3 | 7.24 | 3.89 | 0.32 | N.T. |
| CYP-PA4 | 1.55 | 0.43 | 0.07 | N.T. |

Example 8

Hippocampal Slice Assays

The ability of CYP-PA1 and CYP-PA2 to protect against hypoxic injury in neurons of the CA1 region of the hippocampus was examined, using an assay which involves intact tissue sections taken from the hippocampal regions of rat brains. To carry out these assays, male Sprague-Dawley rats were briefly anesthetized with halothane and decapitated. Brains were quickly removed and placed in cold artificial cerebral spinal fluid (ACSF) for one minute. ACSF was composed of (in mM): NaCl, 126; KCl, 4; $KH_2PO_4$, 1.4; $MgSO_4$, 1.3; $CaCl_2$, 2.4; $NaHCO_3$, 26; and glucose, 4; pH 7.4, saturated with 95% $O_2$, 5% $CO_2$. Hippocampi were dissected free from the brains, and cut into 475 $\mu$m transverse sections (also called slices). The slices were placed in paired recording wells perfused with ACSF maintained at 37° C. Several hippocampal slices were placed in each recording well.

One hour after placement of the tissue slices into recording wells, the orthodromic CA1 population spike (PS) was measured. This indicator of synaptic and neuronal cell body function was elicited by stimulation with a twisted bipolar electrode placed over the CA3 Schaffer collaterals. Responses were recorded in the pyramidal layer of CA1, using a tungsten electrode. Strengths of currents and recording electrode depth were adjusted to obtain maximal amplitude of the CA1 PS. Only slices having an orthodromic CA1 PS of 3 mV or greater on initial assessment were used for further testing.

One tissue slice in each well was given orthodromic stimulation every 30 seconds throughout the experiment, in order to monitor evoked response activity. These slices were designated as "stimulated slices." In general, periodic stimulation provides an even more rigorous test of neuroprotective ability, since the repeated stimulation forces neurons to use up their metabolic resources after each impulse, to reestablish a polarized and ready-to-fire status.

For the remaining slices in each well, orthodromic and antidromic PS amplitude was assessed at the beginning and end of each experiment, without any periodic stimulation. These slices were designated as "unstimulated slices."

All slices were subjected to hypoxia by changing the perfusion medium to oxygen-devoid ACSF saturated with 95% $N_2$, 5% $CO_2$. Slices in one recording well additionally received exposure to various concentrations of the poly-guanidino compounds discussed above, added directly into the perfusion ACSF. Hypoxic duration was continued until 5 minutes after the disappearance of the hypoxic injury potential (Fairchild et al 1988) in the unmedicated stimulated slice. Final recovery was assessed 60 minutes after returning to oxygenated conditions. Exposure to the poly-guanidino compounds began 30 minutes prior to hypoxia and continued through the first 15 minutes of recovery.

For the compounds tested, the concentrations (in micromolar units) which elicited a 50% recovery ($EC_{50}$) of CA1 orthodromic or antidromic PS amplitude, compared to paired but untreated slices, are given in Table 2, for both stimulated and unstimulated slices.

TABLE 2

$EC_{50}$ VALUES (MICROMOLAR) FOR RADIAL POLY-GUANIDINO COMPOUNDS IN HIPPOCAMPAL SLICE TESTS

| | STIMULATED SLICES | | UNSTIMULATED SLICES | |
|---|---|---|---|---|
| | orthodromic PS amplitude | antidromic PS amplitude | orthodromic PS amplitude | antidromic PS amplitude |
| CYP-PA1 | 97 | 95 | 90 | 87 |
| CYP-PA2 | 43 | 42 | 38 | 37 |

These data indicated that: (i) both compounds can provide substantial neuroprotective activity; and (ii) the hexa-arginine compound, CYP-PA2, was somewhat more potent than the tri-arginine compound, CYP-PA1.

Example 9

Toxicity Testing of the Candidate Compounds

At about the same time that the hippocampal slice assays were being conducted, toxicity tests also were being conducted, using conventional $LD_{50}$ tests (i.e., "lethal dosage" tests, which determine the dosage level that is lethal to 50% of the animals receiving that dosage). These tests used intraperitoneal (IP) injection in mice.

The results indicated that the CYP-PA2 compound had an $LD_{50}$ level of 125 mg of drug per kg of body weight. By contrast, when the CYP-PA1 compound was tested for toxicity, it showed no detectable lethal or other adverse effects, even at the highest dosage tested (200 mg/kg).

Accordingly, most of the subsequent in vivo tests focused on the CYP-PA1 compound, rather than the CYP-PA2 compound.

Example 10

In Vivo Protection Against Global Brain Ischemia

Adult male Mongolian gerbils, 50 to 60 grams body weight, were put under methoxyflurane anesthesia and surgically subjected to reversible bilateral carotid occlusion for 5 minutes, using published methods (Wasterlain et al 1996). Occlusion was produced by exposure of both common carotid arteries via a ventral midline incision, isolation of the carotids with 4-0 silk suture, and application of microaneurysm clips. After five minutes of occlusion, the clips were removed, and the incision was closed. Body temperature was maintained at 37° C. throughout the surgical and recovery periods.

Blockage of both common carotids generates global brain ischemia in most gerbils. However, some gerbils contain a vascular structure at the base of the brain which resembles the Circle of Willis in humans, which allows some commingling of oxygenated blood from the carotid and vertebral arteries. Accordingly, the surgical method of generating global ischemia in gerbils by clamping flow through the carotids is not completely reliable in all test animals. To overcome this problem, a sufficient number of gerbils must be treated and tested to ensure statistically significant and reliable results.

A solution containing the test compound (or saline, as a control) was administered at the dosage and time described below, via intraperitoneal (IP) injection. The gerbils were sacrificed 72 hours later, and the brains were perfusion-fixed with paraformaldehyde. Serial sections of the brain were cut and stained with hematoxylin and eosin, and quantitative cell counts of live and dead neurons in the CA1 and CA2 fields of the hippocampus and in the subiculum were made, using both light and fluorescence microscopy. Evaluation of neuronal damage in other brain regions was also made on a semi-quantitative scale, and statistical analysis was performed on all damage scores (non-paired Student's T test). Evaluations used double-blinded procedures, wherein the pathologist who examined a section did not know what treatment any gerbil had received.

During the course of these in vivo tests, the results of the toxicity tests described in Example 9 became available. These results raised concerns about potential toxicity of the CYP-PA2 compound; therefore, the in vivo anti-ischemia tests on the CYP-PA2 compound were not as extensive as the anti-ischemia tests which used the CYP-PA1 compound.

The in vivo tests involving the CYP-PA2 compound used two different dosage regimens. One set of test animals received two injections: 30 mg/kg, at 30 minutes prior to the start of ischemia, and another 30 mg/kg at 90 minutes after the termination of ischemia. The results showed good neuroprotective activity; in the untreated control group, 74.6% of the neurons showed visible damage, while only 40.9% of the neurons showed damage in the treated animals. This neuroprotective activity was statistically significant at higher than the 95% level. A second set of test animals received a smaller dosage (10 mg/kg) of CYP-PA2, in a single injection 30 minutes before the onset of ischemia. In these animals, 56.1% of the neurons were damaged, compared to the 74.6% damage level in the untreated controls. This reduction did not reach the 95% confidence level, in statistical significance.

Tests on the CYP-PA1 compound used three different dosage levels: 7.5 mg/kg, injected 30 minutes before occlusion began; 20 mg/kg, injected 30 minutes before occlusion began; and 20 mg/kg, injected 30 minutes after occlusion was terminated.

In all treatment dosages, the number of injured neurons was substantially reduced when compared to saline-treated control animals, as shown in Table 3. The values reported in Table 3 are median numbers of visibly damaged neurons, counted in a single entire tissue slice. Reductions in neuronal damage levels were significant at the 98% level or higher in the subiculum and CA1 regions. Since the CA2 region is not highly susceptible to ischemic damage, the baseline damage levels in the control animals were not high, and reductions in damage levels by the CYP-PA1 drug did not rise to the level of significance at the 95% confidence level, even though reduced damaged levels were apparent in the CA2 region.

TABLE 3

REDUCTION OF NEURONAL DAMAGE BY CYP-PA1
USING GLOBAL CEREBRAL ISCHEMIA IN GERBILS

|  | Subiculum | CA1 | CA2 |
| --- | --- | --- | --- |
| Saline controls | 214.0 | 235.5 | 23.9 |
| 7.5 mg/kg pre-occlusion | 91.5 | 37.5 | 15.2 |
| 20 mg/kg pre-occlusion | 38.5 | 18.0 | 10.4 |
| 20 mg/kg post | 31.0 | 14.5 | 14.7 |

It should be emphasized that the reduction of neuronal damage was quite substantial and beneficial, even in the animals that were injected with the CYP-PA1 compound only after the carotid artery occlusion had been terminated. This indicates good promise for the compounds disclosed herein in effectively treating victims of stroke and other forms of cerebral ischemia, since medical treatment in such cases usually cannot be commenced until after the medical crisis has arisen.

It also should be emphasized that the in vivo test methods, which involved injecting the drugs intraperitoneally (i.e., into the abdominal region of the animals) were designed in a way that required the drugs to permeate through the blood-brain barrier (BBB) and contact neurons inside the brain, in order to be effective. The ability to permeate through the BBB in sufficient quantities to exert an actual neuroprotective effect is an important trait of useful neuroprotective drugs.

Example 11

Comparison of D-arginine vs. L-arginine compounds

As mentioned above, polyamine compounds which incorporate the D isomer of arginine, rather than the naturally-occurring L isomer, can be synthesized if desired. Since the D isomers of amino acids do not normally occur inside the mammalian body, compounds that contain the residues of D isomers may have longer half-lives in the blood and greater neuroprotective potency.

During an early stage of the research which led to this invention, while various polypeptide compounds were being evaluated, a number of polypeptide polyamines were generated which allowed direct comparison of the D-arginine forms against the L-arginine forms. These different isomeric forms are listed and compared against each other, in Table 4. In that table, "R" refers to the natural L isomer of arginine;

K stands for lysine, Y stands for tyrosine, and F refers to phenylalanine (these are all standard single-letter amino acid abbreviations). D isomers of arginine are indicated in Table 4 as "dr". In all of these compounds, the carboxy end of the amino acid was capped by coupling an $NH_2$ group to it, to form an amide group.

TABLE 4

COMPARISON OF D AND L ARGININE ISOMERS IN CHANNEL-SPECIFIC LIGAND BLOCKING ($IC_{50}$ VALUES, micromolar)

| Compound | G6A (N-type) | M7A (N-type) | M7C (P/Q type) |
|---|---|---|---|
| RRR | 29.90 | 15.80 | 8.70 |
| drdrdr | 22.91 | | |
| RRRRR | 1.95 | 0.98 | 0.27 |
| drRdrRdr | 2.82 | | 0.15 |
| YFRRR | 12.88 | 5.50 | 4.17 |
| YFdrdrdr | 9.33 | | |
| YFRRRR | 2.19 | 1.46 | 0.80 |
| YFdrRdrR | 2.82 | 2.19 | 0.50 |
| YFdrdrdrdr | 2.46 | 1.70 | 0.46 |
| YFRRRRR | 1.95 | 0.98 | 0.45 |
| YFdrRdrRdr | 1.62 | 0.78 | 0.14 |
| YFdrdrdrdrdr | 2.07 | 0.66 | 0.13 |

These results indicate that in most of the compounds tested, the D isomers were more potent than the naturally occurring L isomers, in blocking binding activities of competing ligands at P/Q-type calcium channels in neurons (and, in some cases, at N-type calcium channels as well). Accordingly, D isomers of arginine can be incorporated into any of the neuroprotective arginine-containing compounds disclosed herein, and the resulting "D-isomer" compounds can be evaluated for neuroprotective safety and efficacy, using no more than routine experimentation, by means of assays such as disclosed in Examples 7–10. It is believed that at least some of such D-isomer radial arginine compounds are useful as neuroprotective drugs, as can be evaluated and confirmed for any specific such compound. In addition, it is anticipated that mixtures of L-isomer and D-isomer radial arginine compounds can also be used for neuroprotective purposes, as disclosed herein.

Thus, there has been shown and described a new and useful type of drug for reducing neuronal damage caused by cerebral ischemia or hypoxia. Although this invention has been exemplified for purposes of illustration and description by reference to certain specific embodiments, it will be apparent to those skilled in the art that various analogs, derivatives, and salts of the illustrated compounds can be created and screened for neuroprotective potency, using no more than routine experimentation. Any such equivalents derived from the teachings herein, which do not depart from the spirit and scope of this invention, are deemed to be covered by this invention.

REFERENCES

Bertolino, M., and Llinas, R. R., "The central role of voltage-activated and receptor-operated calcium channels in neuronal cells," Ann. Rev. Pharmacol. Toxicol. 32: 399–421 (1992)

Dunlap, K. et al, "Exocytotic Ca++ channels in mammalian central neurons," Trends Neurosci. 18: 89–98 (1995)

Fairchild, M. D., et al, "A hypoxic injury potential in the hippocampal slice," Brain Res. 453: 357–361 (1988))

Kasai, H., et al, "Presynaptic Ca-antagonist omega-conotoxin irreversibly blocks N-type Ca-channels in chick sensory neurons," Neurosci. Res. 4: 228–235 (1987)

Nowycky, M. C., et al, "Three types of neuronal calcium channels with different calcium agonist sensitivity," Nature 316: 440–443 (1985)

Olivera, B. M., et al, "Calcium channel diversity and neurotransmitter release: The conotoxins and agatoxins," Ann. Rev. Biochem. 63: 823–67 (1994)

Wagner, J. A. et al, "Omega-conotoxin GVIA binding to a high-affinity receptor in brain: characterization, calcium sensitivity and solubilization," J. Neuroscience 8: 3354–3359 (1988)

Wasterlain, C. G. et al, "Felbamate protects CA1 neurons from apoptosis in a gerbil model of global ischemia," Stroke 27: 1236–1240 (1996)

Wheeler, D. B., et al, "Changes in action potential duration alter reliance of excitatory synaptic transmission on multiple types of Ca++ channels in rat hippocampus," J. Neurosci 16: 2226–37 (1996)

We claim:

1. A method of treating a human patient to protect neurons against excitotoxic damage, comprising the step of administering, to a patient in need thereof, a therapeutically effective quantity of a pharmaceutically acceptable neuroprotective polyamine which can penetrate a mammalian blood-brain barrier and suppress entry of calcium ions into central nervous system neurons through both N-type calcium channels and P/Q type calcium channels, wherein the neuroprotective polyamine comprises a molecule having:

a. a center component selected from the group consisting of a nitrogen atom, a carbon atom, stable aromatic rings, stable cycloalkyl compounds, stable heterocyclic compounds, and stable bicyclic ring structures; and, b. at least three branching components which are bonded to the center component and which extend outwardly from the center component, wherein each branching component comprises an arginine residue having a guanidino group, wherein the arginine residue is bonded to the neuroprotective polyamine in a manner that allows the guanidino group of the arginine residue to interact with N-type and P/Q-type neuronal calcium channels in a manner which suppresses calcium ion entry into central nervous system neurons through the N-type and P/Q-type neuronal calcium channels.

2. The method of claim 1, wherein each arginine residue is coupled to the center component through a spacer chain, in a manner which increases accessibility of the guanidino group of the arginine residue.

3. The method of claim 2, wherein each spacer chain comprises from one to about seven carbon atoms.

4. The method of claim 1, wherein the center component consists of a center nitrogen atom and the neuroprotective polyamine comprises three branching components, wherein each branching component comprises an arginine residue.

5. The method of claim 4, wherein each arginine residue is coupled to the center nitrogen atom through a spacer chain, in a manner which increases accessibility of the guanidino group of the arginine residue.

6. The method of claim 1, wherein the center component comprises a center carbon atom and the neuroprotective polyamine comprises four branching components wherein each branching component comprises an arginine residue.

7. The method of claim 6, wherein each arginine residue is coupled to the center carbon atom through a spacer chain, in a manner which increases accessibility of the guanidino group of the arginine residue.

8. A method of treating a human patient to protect neurons against excitotoxic damage, comprising the step of administering, to a patient in need thereof, a therapeutically effective quantity of a pharmaceutically acceptable neuroprotective polyamine which can penetrate a mammalian blood-brain barrier and suppress entry of calcium ions into neurons through both N-type calcium channels and P/Q type calcium channels, wherein the neuroprotective polyamine comprises:

a. a center component selected from the group consisting of a nitrogen atom, a carbon atom, stable aromatic rings, stable cycloalkyl compounds, stable heterocyclic compounds, and stable bicyclic ring structures; and, b. at least three branching components which are bonded to the center component and which extend outwardly from the center component, wherein each branching component contains a spacer chain and a guanidino group, wherein each spacer chain is bonded at a first end to the center component and is bonded at an opposed second end to the guanidino group, in a manner which increases accessibility of the guanidino group and allows the guanidino group to interact with N-type and P/Q-type neuronal calcium channels in a manner which suppresses calcium ion entry into neurons through the N-type and P/Q-type neuronal calcium channels.

9. The method of claim 8, wherein each spacer chain comprises a molecular chain containing from one to about seven carbon atoms.

10. The method of claim 8, wherein the center component consists of a nitrogen atom and the neuroprotective polyamine comprises three branching components, wherein each branching component comprises an arginine residue.

11. The method of claim 8, wherein the center component comprises a carbon atom and the neuroprotective polyamine comprises four branching components wherein each branching component comprises an arginine residue.

12. A neuroprotective polyamine, comprising a polyamine molecule which can penetrate a mammalian blood-brain barrier and suppress entry of calcium ions into central nervous system neurons through both N-type calcium channels and P/Q type calcium channels in a manner which is pharmacologically acceptable and therapeutically effective in reducing excitotoxic brain damage under conditions of cerebral hypoxia, wherein the polyamine molecule comprises:

a. a center component selected from the group consisting of a nitrogen atom, a carbon atom, stable aromatic rings, stable cycloalkyl compounds, stable heterocyclic compounds, and stable bicyclic ring structures; and, b. at least three branching components which are bonded to the center component and which extend outwardly from the center component, wherein each branching component comprises an arginine residue having a guanidino group, and wherein each arginine residue is bonded to the polyamine molecule in a manner that allows the guanidino group of the arginine residue to interact with N-type and P/Q-type neuronal calcium channels in a manner which suppresses calcium ion entry into neurons through the N-type and P/Q-type neuronal calcium channels.

13. The neuroprotective polyamine of claim 12, wherein each arginine residue is coupled to the center component through a spacer chain, in a manner which increases accessibility of the guanidino group of the arginine residue.

14. The neuroprotective polyamine of claim 13, wherein each spacer chain comprises from one to about seven carbon atoms.

15. An injectible drug formulation comprising (i) the neuroprotective polyamine of claim 12 as an active ingredient, mixed with (ii) a liquid carrier substance which renders the formulation suitable for intravenous injection into humans.

16. A sterile dehydrated drug preparation, comprising the neuroprotective polyamine of claim 12 in a dehydrated form which can be reconstituted by mixing with a suitable liquid carrier substance, to create a neuroprotective liquid formulation suitable for injection into humans.

17. The dehydrated drug preparation of claim 16, wherein the dehydrated form of the neuroprotective polyamine is prepared by lyophilization.

18. An article of manufacture, comprising (i) a sealed watertight container capable of maintaining sterility of chemical contents therein, and (ii) a sterile dehydrated drug preparation of claim 16, contained within the sealed watertight container.

19. A neuroprotective polyamine, comprising a polyamine molecule which can penetrate a mammalian blood-brain barrier and suppress entry of calcium ions into central nervous system neurons through both N-type calcium channels and P/Q type calcium channels in a manner which is pharmacologically acceptable and therapeutically effective in reducing excitotoxic brain damage under conditions of cerebral hypoxia, wherein the polyamine molecule comprises:

a. a center component selected from the group consisting of a nitrogen atom, a carbon atom, stable aromatic rings, stable cycloalkyl compounds, stable heterocyclic compounds, and stable bicyclic ring structures; and, b. at least three branching components which are bonded to the center component and which extend outwardly from the center component, wherein each branching component contains a spacer chain and a guanidino group, wherein each spacer chain contains from one to about seven carbon atoms and is bonded at a first end to the center component and is also bonded at an opposed second end to the guanidino group, in a manner which increases accessibility of the guanidino group and allows the guanidino group to interact with N-type and P/Q-type neuronal calcium channels in a manner which suppresses calcium ion entry into neurons through the N-type and P/Q-type neuronal calcium channels.

20. An injectible drug formulation comprising (i) the neuroprotective polyamine of claim 19 as an active ingredient, mixed with (ii) a liquid carrier substance which renders the formulation suitable for intravenous injection into humans.

21. A sterile dehydrated drug preparation, comprising the neuroprotective polyamine of claim 19 in a dehydrated form which can be reconstituted by mixing with a suitable liquid carrier substance, to create a neuroprotective liquid formulation suitable for injection into humans.

22. The dehydrated drug preparation of claim 21, wherein the dehydrated form of the neuroprotective polyamine is prepared by lyophilization.

23. An article of manufacture, comprising (i) a sealed watertight container capable of maintaining sterility of chemical contents therein, and (ii) a sterile dehydrated drug preparation of claim 21, contained within the sealed watertight container.

24. A method of treating neuropathic pain, comprising the step of administering, to a patient in need thereof, a pharmaceutically acceptable poly-guanidino compound which can suppress entry of calcium ions into neurons through N-type and P/Q-type calcium channels, wherein the poly-guanidino compound comprises:

a. a center component selected from the group consisting of a nitrogen atom, a carbon atom, stable aromatic rings, stable cycloalkyl compounds, stable heterocyclic compounds, and stable bicyclic ring structures; and, b. at least three branching components which are bonded to the center component and which extend outwardly from the center component, wherein each branching component contains a spacer chain and a guanidino group, wherein each spacer chain is bonded at a first end to the center component and is bonded at an opposed second end to the guanidino group, in a manner which increases accessibility of the guanidino group and allows the guanidino group to interact with N-type and P/Q-type neuronal calcium channels in a manner which suppresses calcium ion entry into neurons through the N-type and P/Q-type neuronal calcium channels, wherein the poly-guanidino compound is administered to the patient in a dosage which is therapeutically effective in reducing neuropathic pain.

25. The method of claim 24, wherein each spacer chain comprises a molecular chain containing from one to about seven carbon atoms.

* * * * *